United States Patent
O'Neill et al.

(10) Patent No.: US 7,286,675 B1
(45) Date of Patent: Oct. 23, 2007

(54) AUDIO SIGNAL PROCESSORS

(75) Inventors: Graham O'Neill, Merthyr Tydfil (GB); Walter Germanovix, Londrina Parana (GB); Christopher Toumazou, Cumnor Hill (GB)

(73) Assignee: Imperial College of Science, Technology & Medicine, London (GB)

( * ) Notice: Subject to any disclaimer, the term of this patent is extended or adjusted under 35 U.S.C. 154(b) by 0 days.

(21) Appl. No.: 09/600,206

(22) PCT Filed: Jan. 8, 1999

(86) PCT No.: PCT/GB99/00055

§ 371 (c)(1),
(2), (4) Date: Nov. 13, 2000

(87) PCT Pub. No.: WO99/35882

PCT Pub. Date: Jul. 15, 1999

(30) Foreign Application Priority Data

Jan. 12, 1998 (GB) .................. 9800585.3
Jul. 27, 1998 (GB) .................. 9816351.2

(51) Int. Cl.
*H03G 9/00* (2006.01)
*H04R 25/00* (2006.01)

(52) U.S. Cl. ............... 381/102; 381/316; 381/320

(58) Field of Classification Search ........... 381/316, 381/320, 105, 102, 98, 101
See application file for complete search history.

(56) References Cited

U.S. PATENT DOCUMENTS

| | | | | |
|---|---|---|---|---|
| 4,400,590 A | * | 8/1983 | Michelson | 607/57 |
| 4,525,857 A | * | 6/1985 | Orban | 381/100 |
| 4,882,761 A | * | 11/1989 | Waldhauer | 381/106 |
| 4,993,073 A | | 2/1991 | Sparkes | |
| 5,168,526 A | * | 12/1992 | Orban | 381/94.8 |
| 5,276,739 A | | 1/1994 | Krokstad et al. | |
| 5,549,658 A | | 8/1996 | Shannon et al. | |
| 5,814,095 A | * | 9/1998 | Muller et al. | 607/57 |
| 5,983,139 A | * | 11/1999 | Zierhofer | 607/56 |
| 6,141,425 A | * | 10/2000 | Murayama et al. | 381/98 |

FOREIGN PATENT DOCUMENTS

WO   WO97/15114   4/1997

OTHER PUBLICATIONS

Ngarmnil, J. et al., "A fully tuneable micropower log-domain filter", IEE Colloquium on Low Power Analogue and Digital VLSI: ASICS, Techniques and Applications, London, Jun. 2, 1995 pp. 9/1-9/4.*

(Continued)

*Primary Examiner*—Xu Mei
(74) *Attorney, Agent, or Firm*—Calfee, Halter & Griswold LLP

(57) ABSTRACT

An audio signal processor includes a tone control (23). The tone control comprises two low-pass filters (221, 222) operating in current-mode and a subtractor (223) which subtracts the output currents of the filters to produce a band-pass characteristic. Each filter is a tuneable log-domain current-mode filter comprising MOS transistors operating in weak inversion. The tone control is useful in audio signal processors, hearing aids and single-channel and multi-channel Cochlear implants.

13 Claims, 17 Drawing Sheets

OTHER PUBLICATIONS

"Cochlear Implants: Technology for the profoundly deaf" by Catherine George, *Measurement & Control,* vol. 26, Nov. 1993, pp. 267-270.

"Entwicklungsstand von auf elektrischer Stimulation beruhenden Innenohrprothesen" by Hochmair-Desoyer, *Biomedizinische Technik,* Jul./Aug. 1989, No. 7/8.

"Micropower log-domain filter for electronic cochlea" by Toumazou, et al., Electronics Letters, No. 22, Oct. 27, 1994.

I.R. Sinclair, "Audio Electronics Reference Book", pp. 373-383 BSP Professional Books, 1989.

R.F. Graf & W. Sheets, "Encyclopedia of Electronics Circuits", vol. 6, pp. 653, McGraw Hill 1996.

J. Markus, "Modem Electronics Circuits Reference Manuals", pp. 61 McGraw Hilll 1980.

D.R. Frey, "Log-domain filtering: an approach to current-mode filtering", IEE Proceedings-G, vol. 140, pp. 406-416, 1993.

D.R. Frey, "Exponential State-Space Filters: A generic current-mode design strategy", IEEE CAS-1, vol. 43, No. 1, pp. 34-42, 1996.

C. Toumazou, J. Ngarnmil and T.S. Lande, "Micropower log-domain filter for electronic cochlea", Electronics Letters, vol. 30, No. 22, pp. 1839-1841, 1994.

W.F. House, Cochlear Implaints: "My Perspective"—Cochlear Implant Monographs.

Horowitz and Hill, The Art of Electronics $2^{nd}$ Edition p. 122.

J. Ngarnmil, C. Toumazou, and T.S. Lande, "A fully tuneable micropower log-domain filter", $21^{st}$ European solid Circuits Conference ESSCIRC'95 France. Sep. 1995.

\* cited by examiner

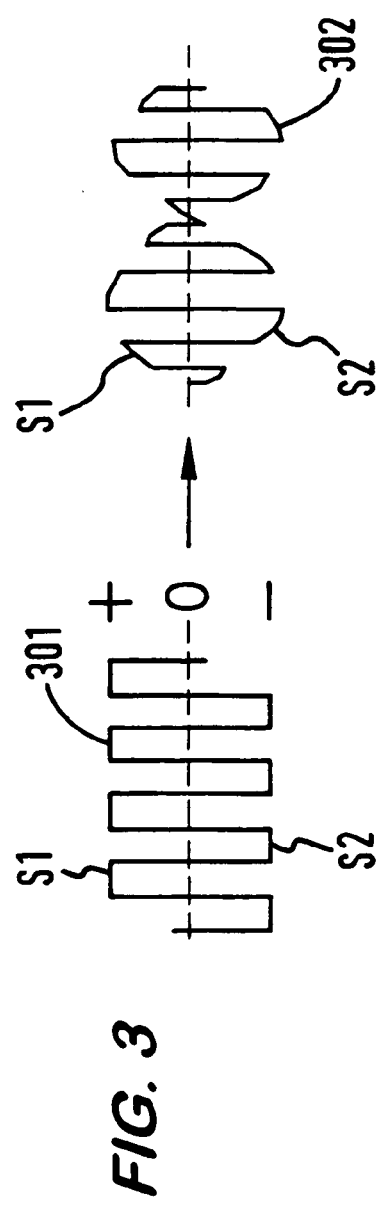
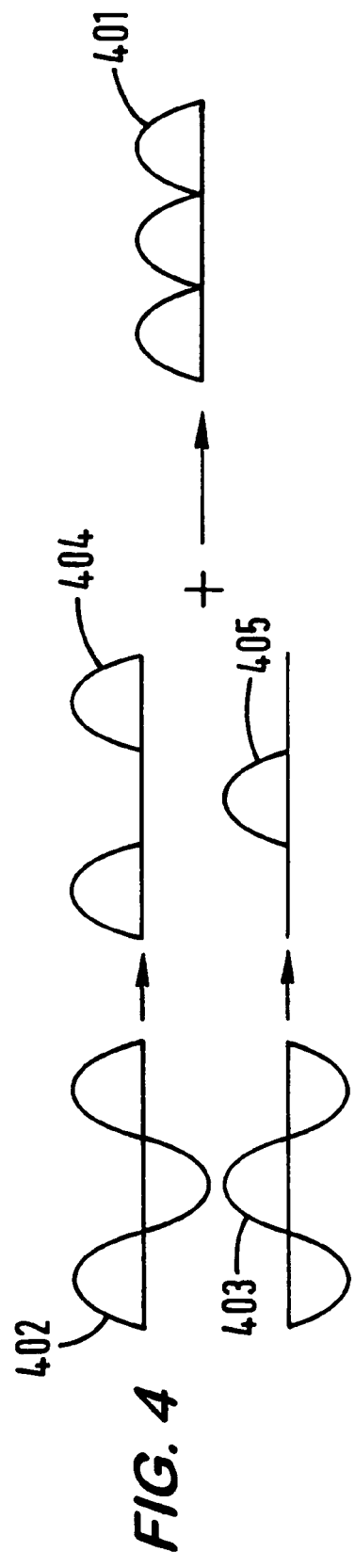
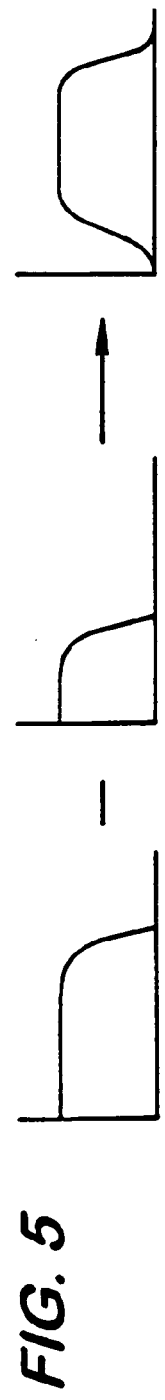
FIG. 3
FIG. 4
FIG. 5

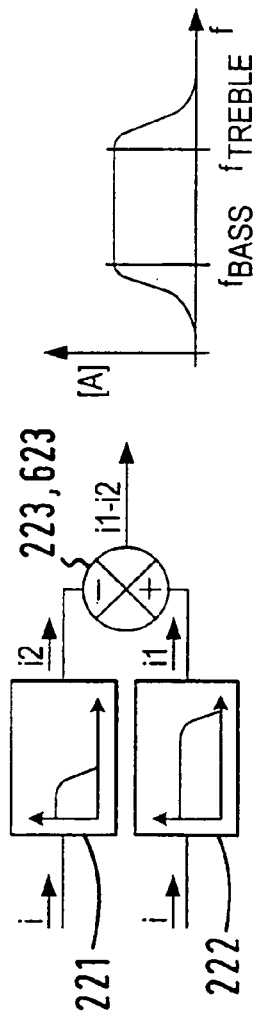
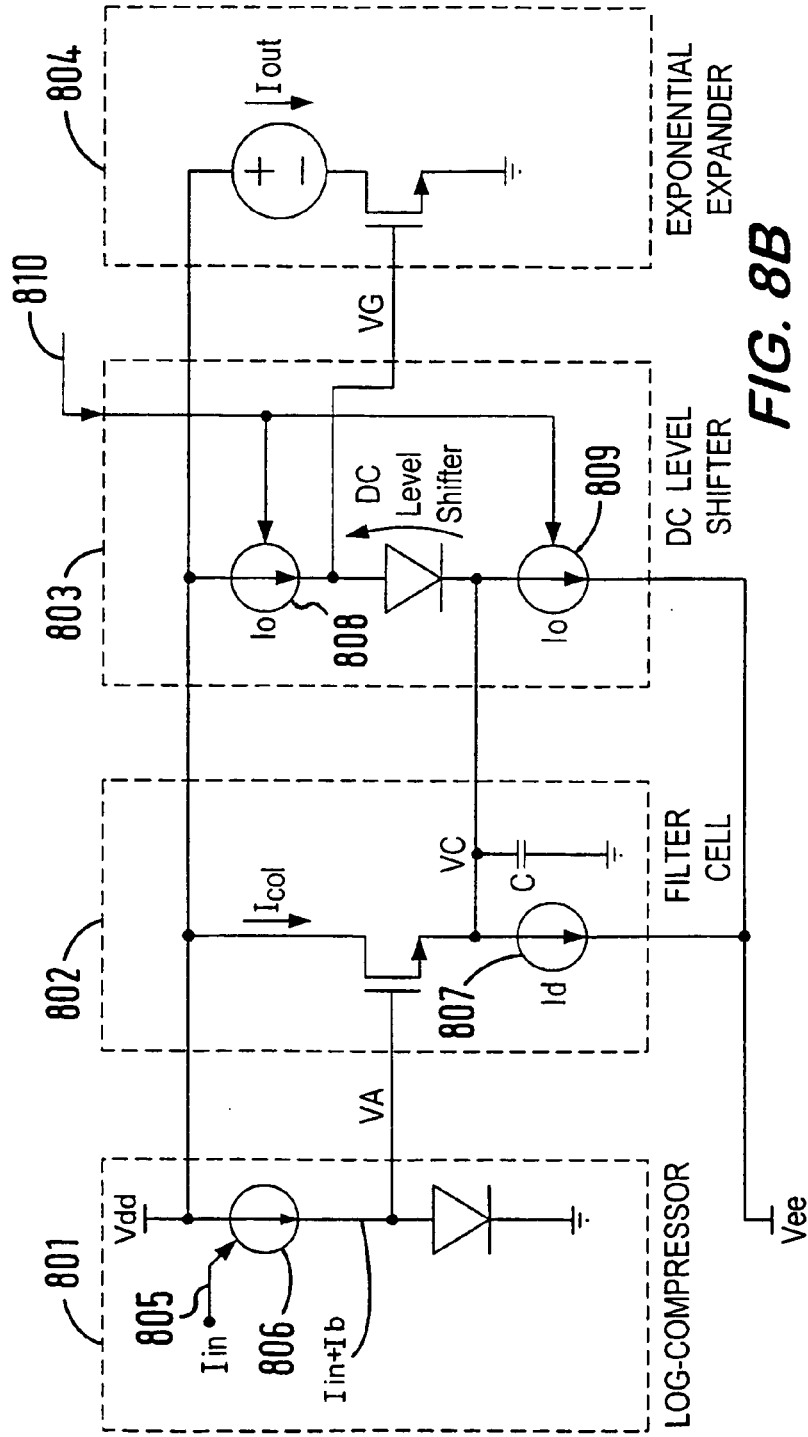
FIG. 8A
FIG. 8B

E+ CELL

E- CELL

AUDIO SIGNAL PROCESSORS

RELATED APPLICATION

This application is a National Stage Application under 35 U.S.C. §371 of International Application No. PCT/GB99/00055, filed Jan. 8, 1999, which both designated and elected the United States and claims priority under 35 U.S.C. §119 to Great Britain Patent Applications Serial Number 9800585.3, filed Jan. 12, 1998, and to Serial No. 9816351.2, filed Jul. 27, 1998, the entire disclosures of which are incorporated by reference herein.

FIELD OF THE INVENTION

The present invention relates to audio signal processors. Preferred embodiments of the invention relate to audio signal processors for use in aural prosthetic devices. Some embodiments of the invention concern audio signal processors for use in hearing aids. Other embodiments of the invention concern audio signal processors for use in Cochlear Implants. Yet further embodiments concern hearing aids and Cochlear Implant.

SUMMARY OF THE INVENTION

Audio Signal Processors, and in Particular, Hearing Aids.

Conventional hearing aids provide considerable help for most individuals with a mild, moderate or severe hearing loss. Whilst modern aids are small and consume little power, there is a desire to further reduce the size and power consumption of hearing aids. In addition it is desirable to produce a simple circuit with reduced cost for a hearing aid. Such a simple circuit would also be applicable to other audio signal processing tasks.

Also, a pre-requisite of all modern hearing-aids is a method of adjustment of the intensity-frequency content of the output of the device in order to compensate appropriately, across the frequency range, for the individual's pattern of hearing loss. For any one frequency, or band of frequencies, this includes device adjustment for both the 'threshold' level of hearing and the 'uncomfortable' loudness level; the difference between these two values being known as the 'dynamic range'. Tone controls are known for various audio applications: see [1], [2] and [3]. In conventional hearing-aids tone control is accomplished by potentiometer-controlled low and high-pass analogue filtering in combination with 'output compression'.

According to one aspect of the invention there is provided an analogue signal processor the analogue processor having an input for receiving an audio signal, an output for delivering a processed audio signal to an audio output transducer, and log-domain filter means comprising MOS transistors operating weak inversion for processing the audio signal. The audio signal is preferably a current signal.

The invention also provides a hearing aid comprising the analogue signal processor of the said one aspect of the invention.

Thus, the invention provides a very low power consumption by virtue of the MOS transistors operating in weak inversion.

Cochlear Implants

Hearing aids are of little help where the deafness is 'profound', that is average loss is greater than about 96 dB in both ears. In such cases an electronic device, surgically implanted in the inner-ear, can provide electrical stimulation to the nerve of hearing, giving the individual a degree of hearing sensation. In some cases open-set speech discrimination is possible, e.g. understanding a telephone conversation.

A Cochlear Implant takes-in environmental sounds, including speech, and converts this into an electrical signal which, by way of for example an implanted wire electrode array, stimulates discrete regions of the inner-ear Cochlea.

From the mid 1980s to around 1990, patients considered suitable for a Cochlear Implant were mainly adults who had, before their deafness, acquired speech and language. They were old enough to understand the implications regarding surgery and post-operative rehabilitation and, having past experience of speech and language, there was considerable potential for a return to an oral communication environment. Gradually, as clinicians around the world became more aware of the benefits of the Cochlear Implant, the focus of attention turned to the profoundly deaf child. From around 1990 onwards, an increasing number of children received a Cochlear Inplant and, in the main, the results have been encouraging.

Because of the success of Cochlear Implants it is expected that, in the future, these devices will even be considered for patients having a greater amount of residual hearing.

Although there have been proposals to provide analogue circuits for use in Cochlear Implants (see [6],[9]) according to the current knowledge of the applicants at present all Cochlear Implants are actually implemented with Digital Signal Processors. Present devices, regardless of manufacturer, are based upon digital technology, for example standard DSP chips and ASICs. The patient wears an external 'speech processor', about the size of a large match-box. This picks-up and processes environmental sounds and passes an electrical signal, via a radio-frequency link, to a 'receiving' device implanted in the ear. This internal receiver sends an electrical signal through a long thin multi-electrode array (up to 22 separate electrodes) within the inner turns of the Cochlea. Thus, the Cochlea is electrically stimulated at discrete sites and the result is a perception of sound. The stimulus intensity, delivered to each channel of the electrode array, needs to be programmed 'channel by channel'. This technology has significant advantages of flexibility, with modifications being achievable through software rather than hardware. The use of a Digital Signal Processor (DSP) provides the manufacturer with the ease of using software to alter various parameters which might be thought important in the development of new processing strategies.

It is desirable to provide in a Cochlear Implants a method of adjustment of the intensity-frequency content of the output of the device in order to compensate appropriately, across the frequency range, for the individual's pattern of hearing loss. For any one frequency, or band of frequencies, this includes device adjustment for both the 'threshold' level of hearing and the 'uncomfortable' loudness level; the difference between these two values being known as the 'dynamic range'. With Cochlear Implants, this output shaping has, up to the present time, been performed by channel-by-channel 'programming'.

The Cochlear Implant designs discussed hereinabove are based upon long, multi-channel electrodes, inserted deep within the Cochlea. The multi-channel design can be used to provide tonotopically distributed information from several processing strategies namely:

i. Continuous Interleaved Sampling—CIS
ii. Feature Extraction or
iii Analogue compression Good results, in terms of open-set speech discrimination have been reported, particularly with the CIS and Feature Extraction strategies.

There are disadvantages associated with Cochlear Implants especially multi-channel implants:— i. Deep insertion of long electrodes can cause considerable damage to surviving neuronal tissue in the diseased cochlea. That is, residual hearing, albeit minimal, is destroyed.

ii. The fitting/programming of current multichannel devices requires channel by-channel adjustment of stimulation levels for both threshold and uncomfortable levels. Considerable expertise is required to programme a 'MAP' which the user feels is the most useful. With current Cochlear Implants, having between 12 and 22 separate electrodes, this 'channel-by-channel' programming is time-consuming, particularly since the implant has to be re-programmed about 3-4 times over the first 12 months after the operation. Some users, even with appropriate counseling, regularly attend for 'reprogramming', over several years, in the hope that one particular 'programme' will result in almost perfect hearing.

iii. The DSP based technology has significant drawbacks of high power consumption and physical size With the current digital devices batteries need changing every few (e.g. 1-2) days or even more frequently, and many patients are unhappy about wearing a relatively large speech processor, although smaller 'behind-the ear' digital processors have reached a fairly advanced stage of development.

iv. Hardware costs are high (approximately £15,000).

The use of a short electrode, single channel system has been advocated by House [7]. He argues that such a system has advantages over a 'long electrode' design in that— i. A short single intra-cochlea electrode will significantly reduce the possibility of damage to residual hearing.

ii. The system design is simple and relatively inexpensive (about ⅓ the cost of a multichannel system)

iii. Power consumption is low, and a head-worn processor can be used.

iv. Fitting/programming is easier and quicker than with multichannel devices.

The articles [6] and [9] disclose an analogue log-domain low-pass filter implemented in MOS technology and having MOS transistors working in weak inversion. The articles propose the use of such filters in an electronic Cochlear prosthesis.

According to another aspect of the present invention, there is provided an analogue audio signal processor for use in a cochlear implant, the processor comprising:

an input for receiving an audio signal, an output for delivering a processed audio signal to a cochlear implant electrode, and a tone control circuit for adjusting the intensity-frequency content of the audio signal fed to the output and comprising first and second filters having different low-pass bands and a subtractor for subtracting the output currents of the filters to produce band-pass filter characteristic, each of the first and second filters being log-domain filters comprising MOS transistors operating in weak inversion.

The audio signal is preferably a current signal.

The invention involves the use of analogue electronics in a way which allows realisation of an extremely small processor with a very low power requirement. Weak inversion or sub-threshold mode of operation of MOS transistors results in an exponential characteristic (or a natural logarithmic characteristic) which is compatible with the exponential characteristic of the Cochlear. Although we envisage the processor being kept external (e.g. behind-the-ear), the invention does, theoretically, allow consideration of a totally implantable device. This is not true of even the most modern developments in digitally-based devices. If the tone control is implanted in the Cochlear, adjustment of the frequency response is performed by wireless remote control. The tone control allows the user for the first time in cochlear implants to control the frequency/intensity content of the audio signal.

According to a further aspect of the invention, there is provided an analogue audio signal processor for use in a cochlear implant prosthesis, comprising an input for receiving an audio signal, a plurality of outputs for connection to respective cochlear implant electrodes, for delivering processed audio signals thereto, and a tone control common to all the outputs for simultaneously adjusting the intensity/frequency content of processed audio signals fed to the said outputs, the tone control comprising MOS transistors operating in weak inversion.

According to a yet further aspect of the invention, there is provided a single channel audio signal processor for use in a Cochlear prosthesis, and including a tone control comprising a log-domain filter having MOS transistors operating in weak inversion, and means controllable by the user of the prosthesis for adjusting the frequency response of the tone control.

According to yet another aspect of the invention, there is provided a multi-channel channel audio signal processor for use in a Cochlear prosthesis and including a tone control common to all the channels at least the frequency response of which is controllable by the user.

We believe that for adults at least, and with the appropriate professional support, giving the user the ability to adjust the tonal quality of their device would be a significant step towards simplifying device re-programming after the initial fitting. We also believe that by this means the user would more readily accept the limitations of the implant and not, as is the case with some, become frustrated with the clinician's attempts at re-programming to reach a quality of sound perception which is, perhaps, for them, unachievable. To this end, our Cochlear Implant design, unlike other current designs, incorporates a 'tone-control', providing easy and rapid frequency shaping of the output. This constitutes a new innovation in Cochlear Implants. Also the use of a tone control common to all the channels of a multi-channel Cochlear Implant allows the instant and simultaneous adjustment of all the channels.

According to yet another aspect of the invention, there is provided analogue multi-channel audio signal processor for use with a Cochlear Prosthesis and comprising an input for receiving an audio signal, a plurality of outputs for connection to respective Cochlear Implant electrodes, a plurality of analogue, signal processing channels coupled to the said input and each comprising a log-domain filter having MOS transistors operating in weak inversion, the channels being coupled to respective ones of the outputs, the intensity/frequency response of each channel being adjustable, and means for adjusting the intensity/frequency response of each channel.

Thus, a multi-channel audio signal processor for use in a cochlear prosthesis is provided, having a small size and low power consumption.

The adjustment of each filter allows the patient to adjust the processor him or her self. Preferably the adjusting means is a wireless remote control. Preferably the remote control has buttons for selecting respective ones of the channels. Most preferably, the patient adjusts the gain (volume) of the chosen channel between the threshold and uncomfortable levels of sound intensity. The patient may be able to vary filter frequency of a channel in some embodiments. The patient may need the assistance of a skilled technician to guide him or her in the adjustment.

Thus, this aspect of the invention allows the patient to control the processor him or her self (albeit with some guidance from a technician). This simplifies reprogramming after initial fitting and the patient may more readily accept the limitations of the Cochlear Implant According to a yet further aspect of the invention, there is provided a current mode analogue tone control circuit for use in an audio signal processor, the tone control comprising MOS transistors operating in weak inversion. Such a tone control provides reduced size and power consumption. The audio signal processor may be an aural prosthetic device.

BRIEF DESCRIPTION OF THE DRAWINGS

For a better understanding of the present invention and to show how the same may be carried into effect, reference will now be made by way of example to the accompanying drawings in which:—

FIGS. 3 to 5 are diagrams illustrating the operation of the prosthesis of FIG. 2;

FIGS. 8A to C are diagrams of an inventive tone control circuit suitable for use in the hearing aid of FIG. 1, or the prosthesis of FIG. 2 or 6;

DETAILED DESCRIPTION

Hearing Aid

Figure 1:
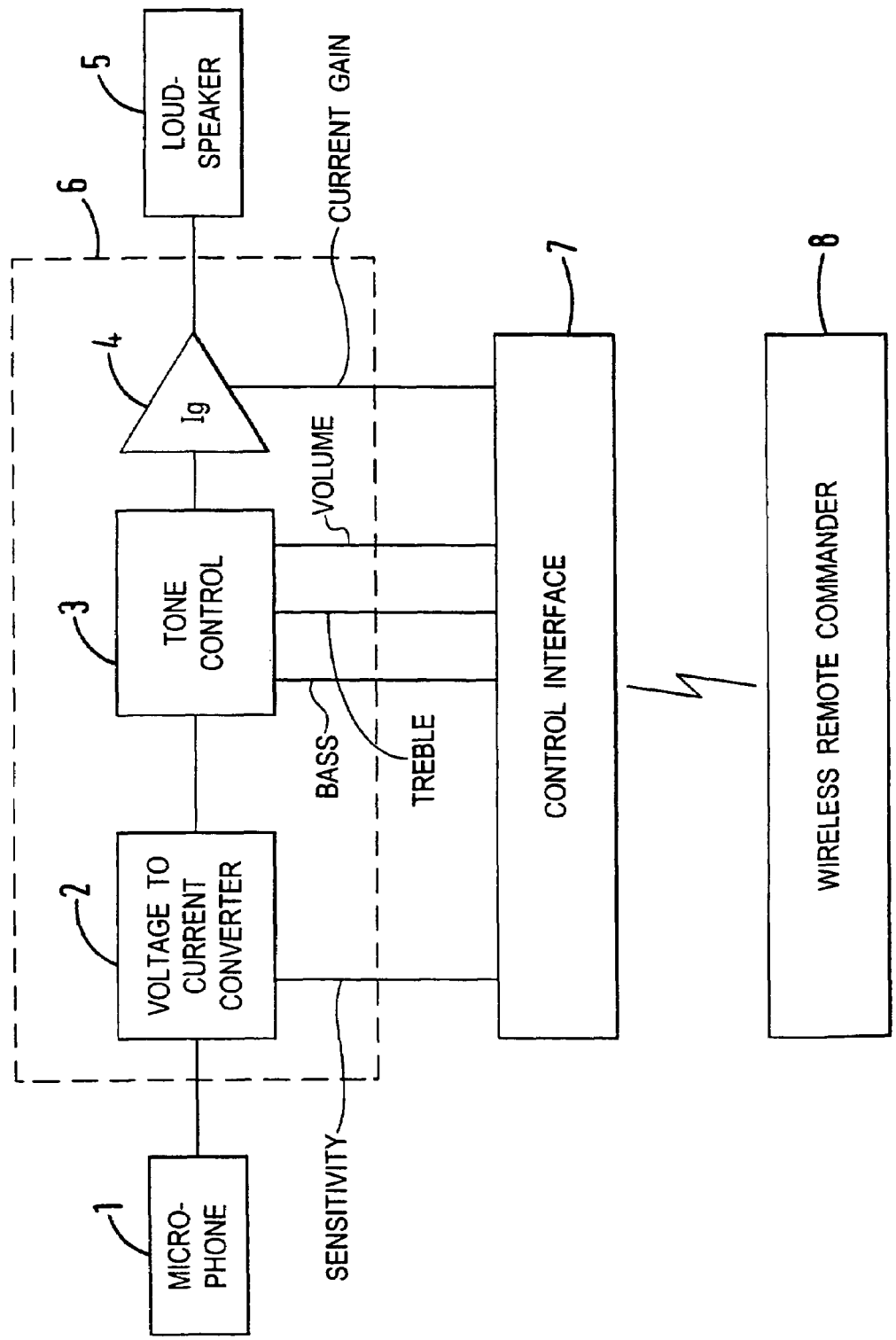
FIG. 1 is a schematic block diagram of an illustrative hearing aid in accordance with the invention.

Referring to FIG. 1 an illustrative hearing aid according to the invention comprises a microphone 1, a voltage to current converter, which is also a compressor, 2, a tone control 3 according to the invention, a current amplifier 4, and a loudspeaker 5 preferably in the form of an earpiece. The hearing aid operates entirely in the analogue domain. The microphone 1 produces audio signals having a particular dynamic voltage range but the ear requires a different, smaller, dynamic range. The compressor 2 compresses the dynamic range and converts the voltage to current. The compressor 2 may also provide sensitivity control controllable by the user. The tone control 3 is controllable by the user and allows adjustment of bass, treble and volume. The tone control 2 feeds the compressed current frequency adjusted by the tone control to the earpiece 5 via the high gain current amplifier 4, which may have a current gain control.

The compressor 2, which will be described hereinafter with reference to FIGS. 11 and 12, comprises CMOS transistors operating in weak inversion. The compressor preferably has a sensitivity control which controls the slope (gain) of the transfer function of the compressor as shown in FIG. 12.

An example of the tone control 3 is shown in FIG. 8 and will be described hereinafter. The tone control is an analogue circuit comprising field effect transistors operating in weak inversion. It provides adjustment under the control of the user of the frequency response of the hearing aid and of volume.

The current amplifier 4 also comprises field effect transistors operating not in weak inversion mode, but with very small currents. The amplifier 4 amplifies the very small current (e.g. nano-amps) output by the tone control 3 to a current (e.g. micro-amps) sufficient to activate the earpiece.

The compressor 2, the tone control 3 and the amplifier 4 may be integrated into a single analogue Integrated Circuit indicated by box 6.

The hearing aid of FIG. 1 has extremely low power consumption and allows the user to control at least the frequency response and volume. The hearing aid may be controlled, via an interface 7, by a wireless remote commander 8.

The audio signal processor of FIG. 1 may be used for audio signal processing in applications other than hearing aids.

Single Channel Cochlear Implant

Figure 2A:
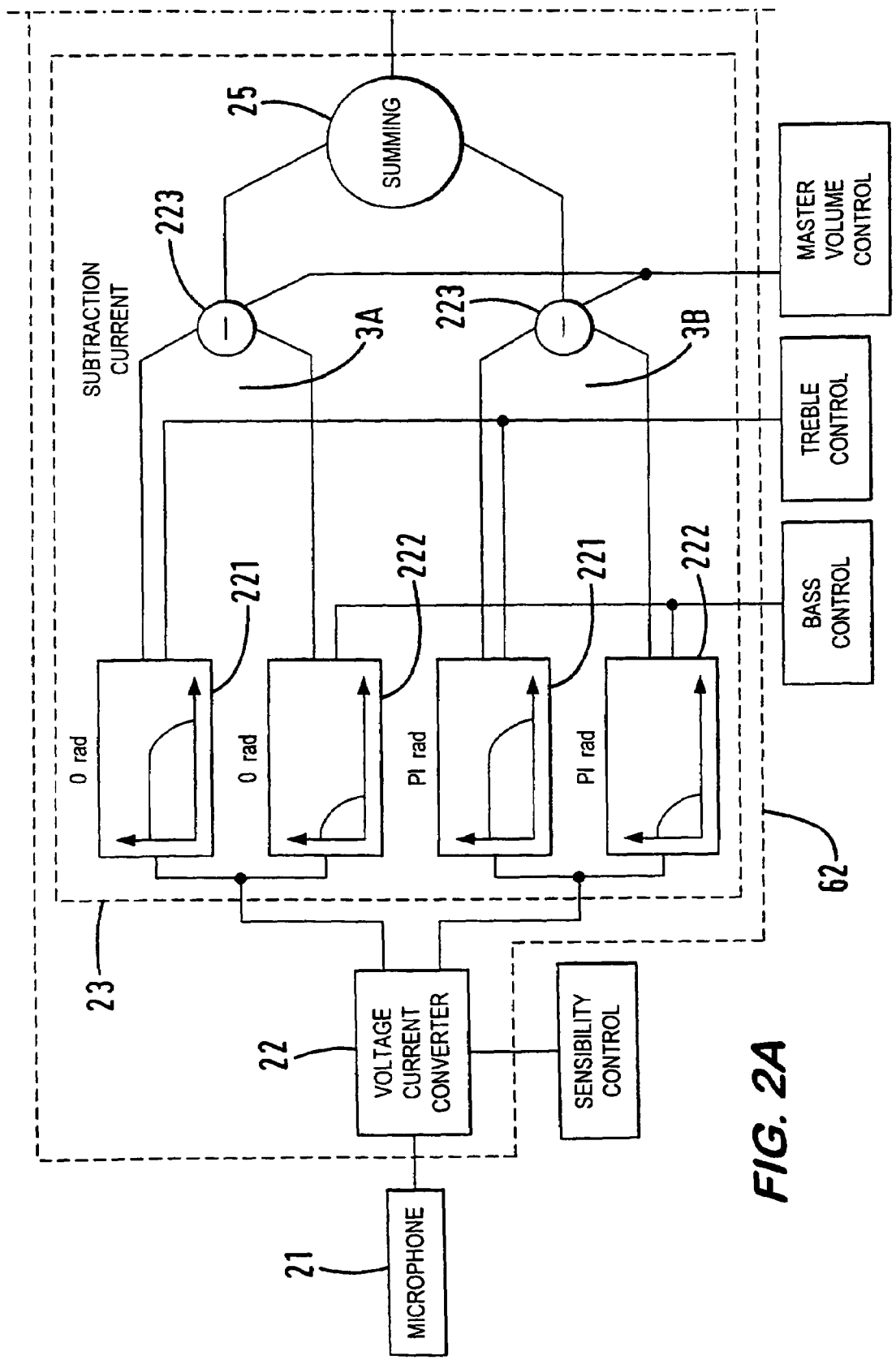
FIG. 2 is a schematic block diagram of an illustrative single channel Cochlear Implant prosthesis.
Figure 2B:
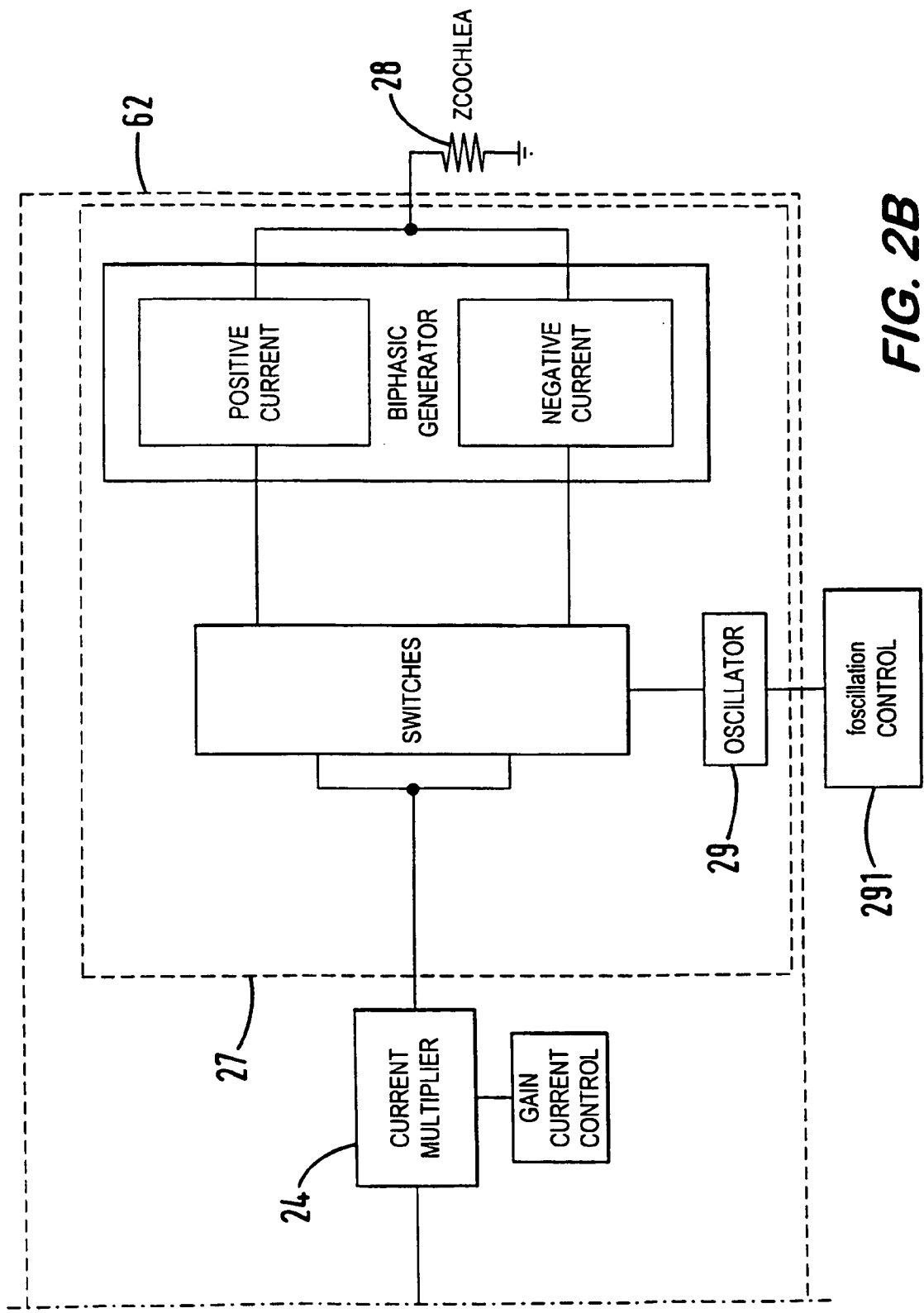

FIG. 2 shows an illustrative example of a single channel Cochlear Implant according to the invention. This single channel embodiment of the invention operates entirely in the analogue domain.

A microphone 21 produces audio voltage signals which are fed to a compressor 22 which converts the voltage signals to audio current signals. The compressor circuit 22 process the signal into a certain dynamic range appropriate for the specific individual. The dynamic range of the output current is controlled by the compressor. The dynamic range that contains most of the area of speech sounds is from about 40 dB to 80 dB and, the dynamic range for electrical stimulation is narrow, in the region between 2 dB and 20 dB varying from individual to individual. In order to perform the electrical compression of the signal the compressor 22 converts voltage to current. That is, the dynamic range of voltage is converted into the dynamic range of current. Here, dynamic range stands for the range between the threshold and uncomfortable levels of hearing. An example of a compressor is shown in FIG. 11. Preferably the compressor allows the adjustment of the dynamic current range by means of a current control. In this example the VIC acts as a sensitivity as well. The amplifier/compressor 2 is implemented by an MOS circuit operating in the weak inversion mode. Because the weak inversion mode is exponential (or natural logarithmic) in characteristic, it effects compression in a manner compatible with the exponential characteristic of the Cochlear.

A tone control 32 allows the user to adjust the frequency response of the system whilst the system is in use:—that has not been possible before in a Cochlear Prosthesis. A circuit useful in the tone control will be described with reference to FIGS. 8 and 9. A current amplifier 24, having a current gain control, amplifies the current output by the tone control 23 and provides it to a biphase signal generator 27 which applies a biphase current to a single implantable electrode 28.

Referring to FIG. 3, a biphase signal is a sampled signal having successive samples each comprising sub-samples S1 and S2 etc. of opposite polarity; that is a positive current pulse followed by a negative current pulse. The samples are of the audio signal produced by the tone control and the current amplifier. A biphase signal is needed to energize an electrode implanted in the Cochlea because applying only pulses of one polarity desensitizes the nerve endings. In the biphase signal generator 27, an oscillator 29 (which may be controllable) produces a "square wave" voltage 301 oscillating between a positive limit and a negative limit. The amplified output current of the tone control amplitude modulates the square wave 301 to produce the sampled biphase current signal 302. It will be appreciated that for simplicity FIG. 3 is schematic and assumes modulation by a sine wave. The frequency of the biphase oscillator is preferably variable by the patient. The sampling rate may a rate known in the art. Although the sampling rate could comply with Nyquist in practice it is much lower and each sample is a burst of varying audio as shown in FIG. 3 at S! and S2.

Referring to FIG. 4 the signal which amplitude modulates the square wave is a full-wave rectified signal 401 which is produced by the tone control 23 so that the Cochlear implant does not stimulate in a silent environment. Ignoring the effect of the tone control, full wave rectification is achieved by producing two audio currents 402 and 403 of opposite phase, rectifying each (e.g. by shifting the DC levels of the currents) to produce half wave rectified currents 404 and 405 and adding the currents 404 and 405 using an adder 25.

Referring to FIGS. 2, 4 and 5, the currents 402 and 403 of opposite phase are produced by complementary outputs of the compressor 22 and fed to the tone control 23. The tone control includes two identical circuits 3A and 3B (an example of which will be described with reference to FIG. 8). The circuits 3A and 3B process the respective signals 402 and 403. Each circuit 3A and 3B comprises a pair of low pass filters 221 and 222 having different pass bands. A subtractor 223 subtracts the outputs of the two circuits to produce a band-pass filtered signal as shown in FIG. 5. The half wave rectification by DC level shifting may take place in the subtractor 223.

The system of FIG. 2 may comprise a housing containing the microphone 1, amplifier/compressor 22 tone control 23, the amplifier 24 and the biphase signal generator 7 and which is worn by the user. The compressor 22, the tone control 23, the amplifier 24 and the biphase signal generator 27 are preferably integrated into a single chip analogue integrated circuit 62. As will be described with reference to FIG. 10, at least the tone control 23 may be controlled by a wireless remote commander.

Multi-channel Cochlear Implant

Figure 6A:
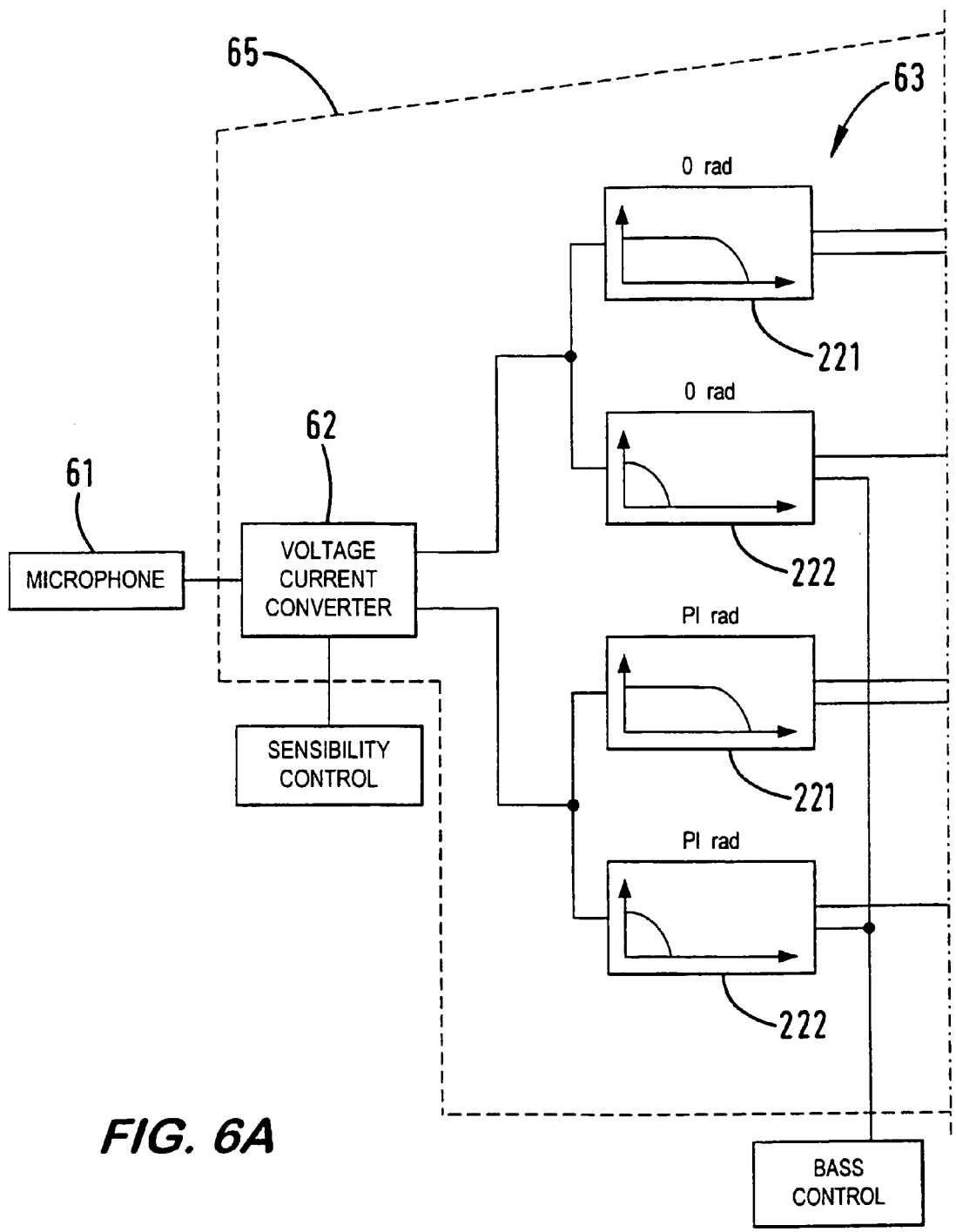
FIG. 6 is a schematic block diagram of an illustrative multi-channel Cochlear Implant prosthesis.
Figure 6B:
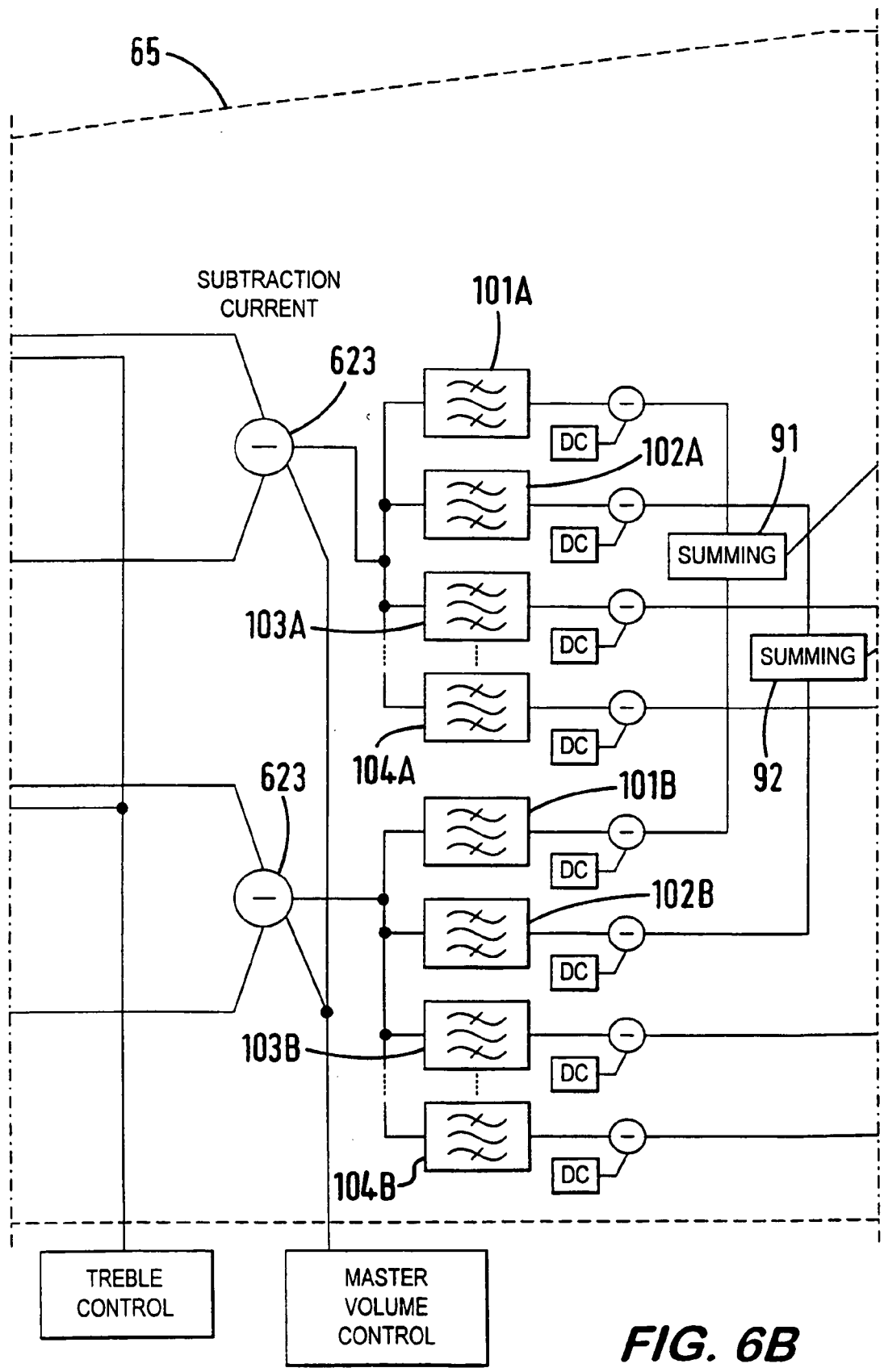
Figure 6C:
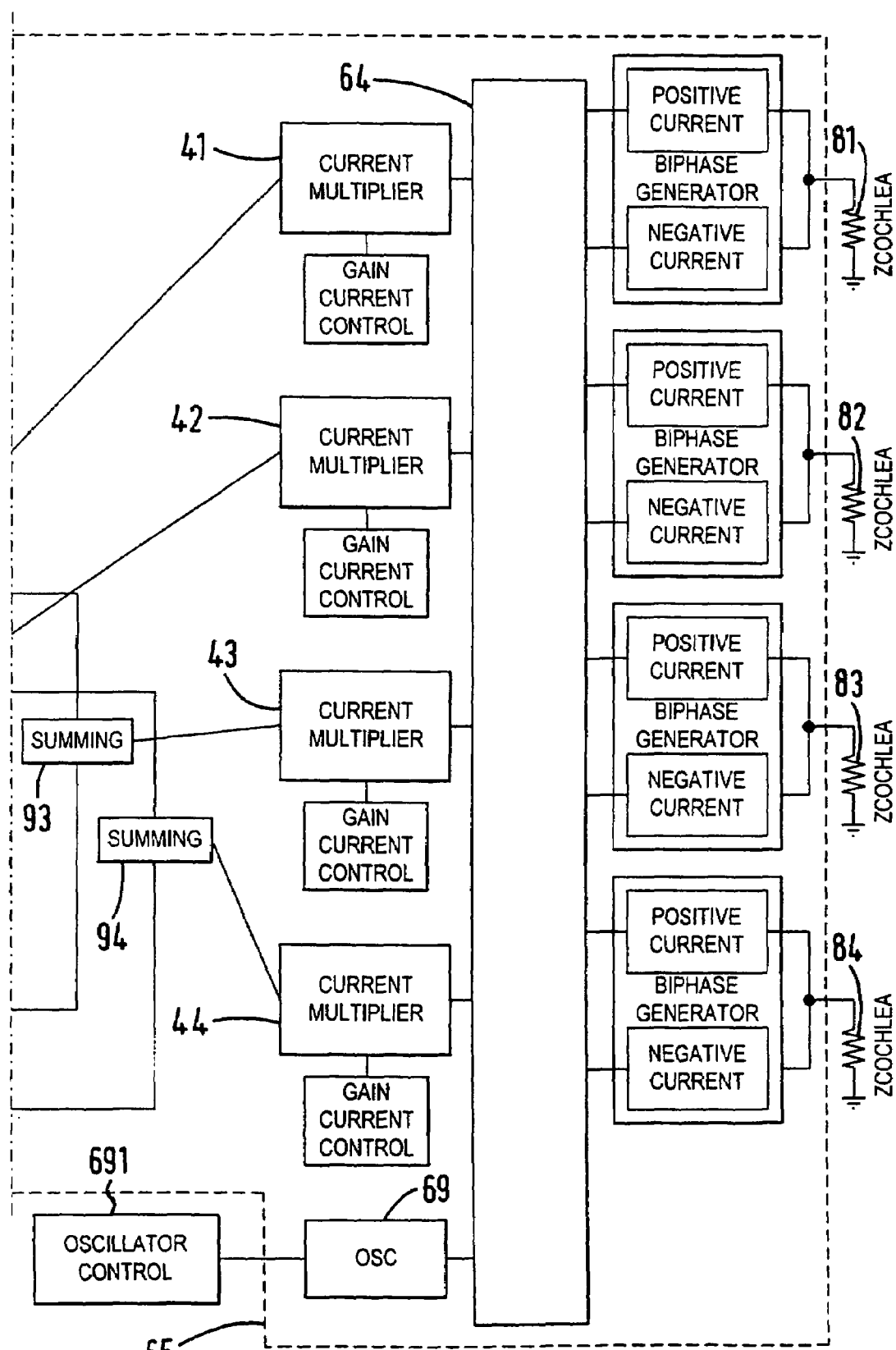

FIG. 6 shows another embodiment of a Cochlear Implant according to the invention and which also operates entirely in the analogue domain. The embodiment is a multi-channel embodiment having an array of electrodes 81 to 84 which in use are implanted in the ear. In the example of FIG. 6 only four channels are shown. In other examples there are at least two channels, and there may be more than four channels. A microphone 61, and compressor 62 similar to those of FIG. 2, produce compressed audio current signals. The compressor 62 is arranged to produce oppositely phased signals on respective outputs. The oppositely phased signals are fed to tone control circuits 3A and 3B as will be described with reference to FIGS. 8 and 9. Each circuit 3A, 3B comprises two low pass filters 221, 222, the outputs of which are fed to respective subtractors 623. Unlike the subtractor 223 of the system of FIG. 2, the subtractors 623 of FIG. 6 produce unrectified, oppositely phased, current signals. The pair of unrectified opposite phase current signals are fed to respective arrays of band-pass filters 101A to 104A and 101B to 104B. Band pass filters 101A and B have the same filter characteristic and produce corresponding filtered signals of opposite phase. The other band pass filters 102A to 104A and 102B to 104B likewise produce correspondingly filtered signals of opposite phase. The band pass filtered signals are fed to half wave rectifiers 11, for example DC level shifting circuits. Corresponding half wave rectified signals of opposite phase are summed in adders 91 to 94 to produce full wave rectified signals which are amplified in respective current amplifiers 41 to 44. The fullwave rectified current signals produced by the amplifiers 41 to 44 correspond to different pass bands defined by the filters 101 to 104.

A circuit comprising MOS transistors, the transistors operating in weak inversion, is preferably used to implement the Band-pass filters 101 to 104 of FIG. 6. An example of a suitable circuit is described with reference to FIG. 13.

Figure 7:
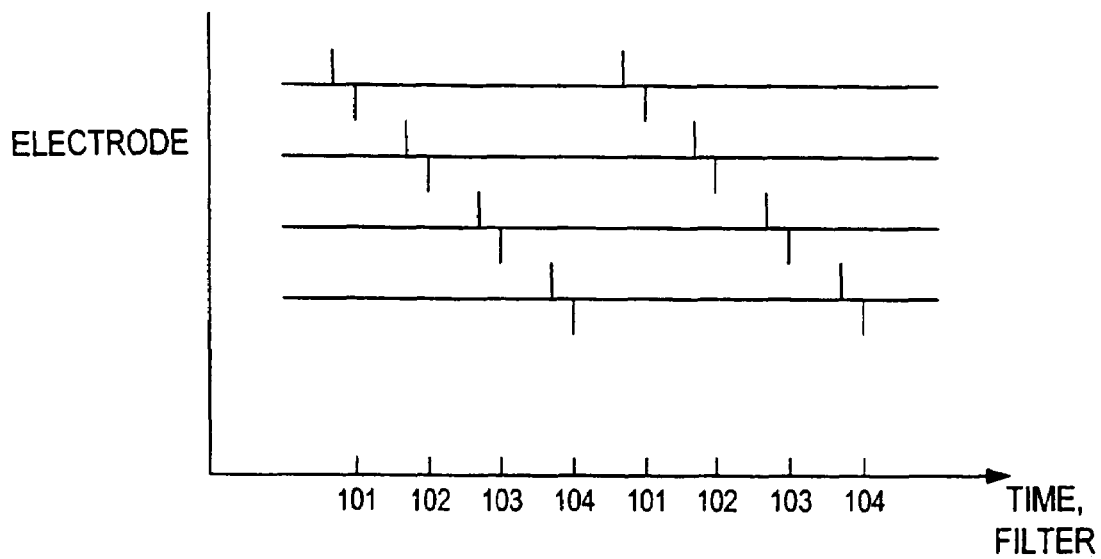
FIG. 7 is a schematic diagram illustrating the operation of a sample interleaving circuit of the prosthesis of FIG. 7.

The fullwave rectified current signals produced by the amplifiers 41 to 44 are fed to an interleaving circuit 12 which samples the signals and interleaves the samples to produce Continuously Interleaved Samples which are biphase modulated and applied to the array of Cochlear Implant electrodes 81 to 84. An oscillator 69 produces a biphase square voltage wave. Referring to FIGS. 6 and 7, there are in effect four channels (in this example) associated with respective pass bands. One channel comprises the pair of band pass filters 101A and B the adder 91 and the electrode 81. The other channels likewise comprise a pair of band pass filters (102A,B; 103A,B; and 104A,B) an adder (92, 93, 94) and an electrode (82, 83, 84). Thus each of the electrodes 81 to 84 is associated with a respective one of the pass bands. The interleaving of the samples is controlled by the interleaving circuit 12. The interleaving circuit activates each channel in turn: when one channel is active all the other channels are inactive. Referring to FIG. 7, the circuit 12 sequentially connects: electrode 81 to filter 101A,B; the electrode 82 to filter 102A,B; the electrode 831 to filter 103A,B; and the electrode 841 to filter 104A,B etc. Each electrode receives a positive and a negative current pulse which together form one sample.

The system of FIG. 6, except for the microphone 61, the controls and the electrodes may be integrated into a single analogue integrated circuit 65.

Various modifications may be made to the Cochlear implants of FIGS. 2 and 6. For instance, the pulses produced by the oscillator 29, 69 may be controlled by a control 291, 691. The pulse repetition rate and/or the pulse widths may be varied. The sampling rate for each electrode may be a rate known in the art for Continuous Interleaved Samples. Although the sampling rate could comply with Nyquist in practice it is much lower and each sample is a burst of varying audio as shown in FIG. 3 at S! and S2.

The design of the illustrative Cochlear Implant prosthesis described with reference to FIGS. 2 and 6 focuses on two areas:

i) Low-Power Electronics:

The system focuses upon a new design of analogue electronics architecture. The core of the design, especially the tone control and the bandpass filters, makes use of CMOS transistors operating in weak inversion. Other parts of the system operate in the micro-power regime and preferably in weak inversion.

ii) 'Tone-Control' for a Single Channel System and for a Multi-Channel System:

In the multi-channel system the tone control is preferably common to all channels to provide instantaneous adjustment over all channels. The tone control is based upon two low pass filters and a current subtractor.

As will be described with reference to FIG. 8, the tone control comprises CMOS transistors which operate in weak inversion (sub-threshold mode) in current mode and the circuit structure is based on the 'log-domain' for building the filters tunable in the audio frequency range.

Tone Control

Figure 8C:
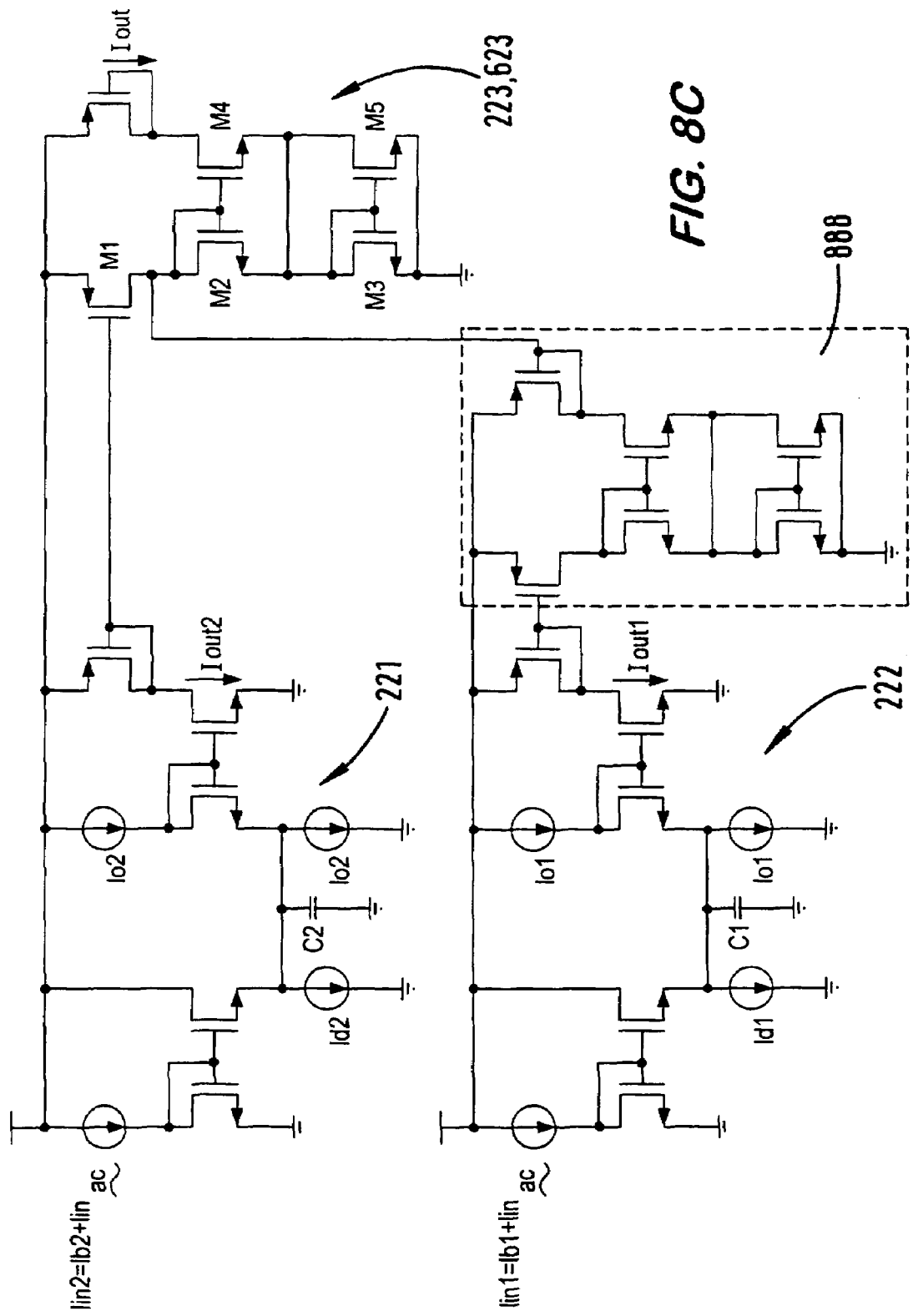
Figure 9A:
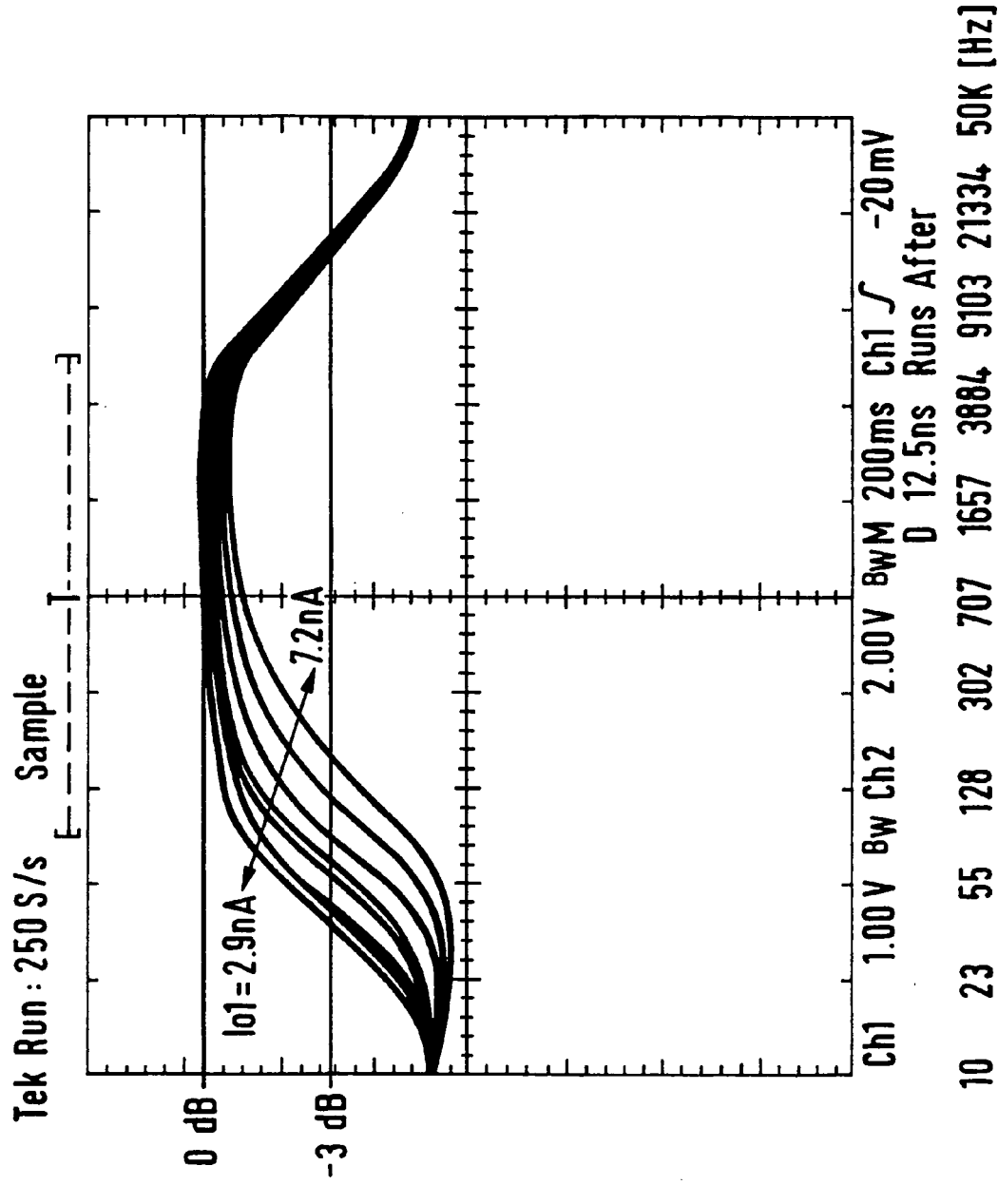
FIGS. 9A and 9B are frequency/amplitude diagrams for the tone control of FIG. 8.
Figure 9B:
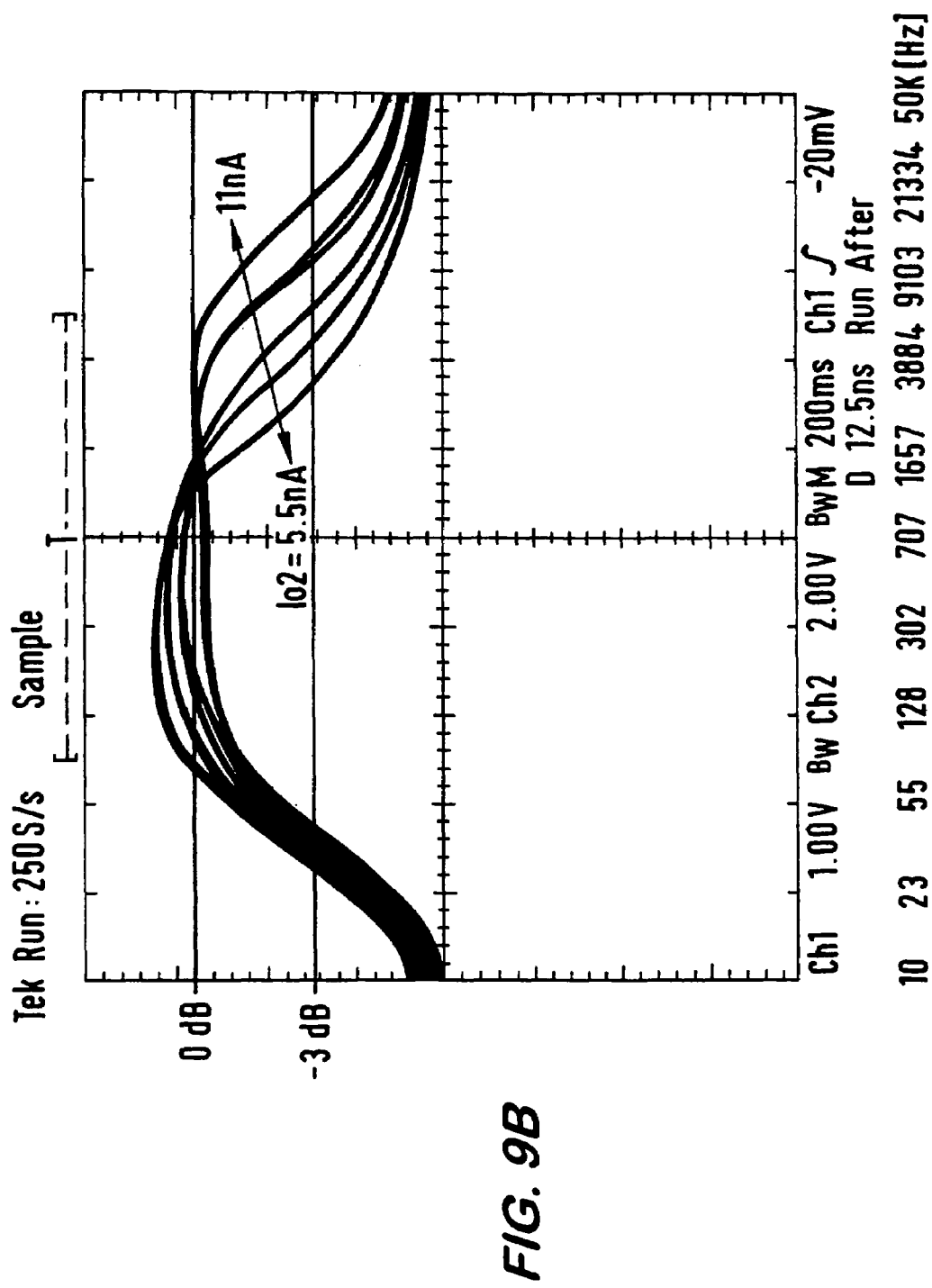

FIGS. 8A to C together show a tone-control circuit useful in the hearing aid of FIG. 1 and in the systems of FIGS. 2 and 6. The tone control as shown in FIG. 8A comprises two first-order log-domain filters 221 and 222 and a subtractor 223 or 623 built with CMOS transistors operating in weak inversion. The tone-controller is capable of providing bass cut/boost and treble cut/boost operation as shown in FIGS. 9A and 9B.

The role of the tone controller is to boost/cut the low/high frequencies of the audio range. This is accomplished by the implementation of a flexible frequency shaping function which facilitates the selective placement of poles and zeros on the complex plane. In the embodiments of the invention shown in FIGS. 2 and 6, the tone-controller is a subsystem of an all-analogue implementation of Cochlear Implant device where physical constraints such as size and power consumption dictate the necessity of its implementation in an analogue very low power environment, particularly without the incorporation of conventional active (e.g. op-amps) or resistive elements. More specifically, even for a diseased Cochlea the hearing sensation depends upon the frequency of the incoming signal. For a diseased Cochlea with greater sensitivity at low frequencies than at high frequencies (or vice-versa) the tone control will act to balance the hearing sensation to a comfortable level. The design of the circuit of FIGS. 8 and 9 is based on the log-domain design technique [4-5] which exploits the intrinsic non-linear (exponential) behavior of a transistor and provides extended dynamic range under low power supply levels. In [6] it was shown that this technique is suited for use with MOS transistors in weak-inversion mode (or sub-threshold mode [8]) of operation. In addition to the wide dynamic range possible with the log-domain technique, the design versatility offered by the implementation provides for ease and flexibility of tuning. In addition the exponential characteristic of MOS transistors operating in weak inversion and the log-domain design matches the exponential response of the Cochlea.

For the specific application for which the tone-controller is intended, a bass-cut treble-cut operation is of primary importance as the controller operates in conjunction with a separate volume control section, for example, the amplifier/compressor 2 or the current multiplier 24, 41-44. Hence a "two pole—one zero" frequency shaping network is appropriate. This is achieved by using a pair of first-order low-pass log-domain filters 221 and 222 which are built by means of MOS transistors operating in weak-inversion and which are tuneable in the audio frequency range. The output signal is the difference produced by a subtractor 223, 623 of the outputs of the two filters.

An example of one of the log-domain filters is shown in FIG. 8B. As is known from [4], [5] and [6], the log-domain filter comprises a log-compressor 801, a filter cell 802, a DC level shift 803, and an exponential expander 804.

The log compressor 801 includes a current source 806 having an input 805 for receiving an input current Iin from the voltage to current converter 2 or 22, Iin is the compressed audio current signal. The current source 806 produces a current Iin+Ib. The filter cell 802 includes a current source 807 producing a current Id. The DC level shifter 803 has current sources 808 and 809 producing currents Io which are controllable by a control input 810.

By selection of Id and Io the filter operates as a low pass filter. By varying Io, the response of the filter is varied as shown in FIG. 9A or 9B.

As shown in FIG. 8C, two filters 221, 222 (each as shown in FIG. 8A) including the current sources are implement entirely in MOS transistors operating in weak inversion. Filter 222 is coupled to the subtractor by a high impedance buffer 888. The output current Iout (s) of the subtractor 223, 623 is given by Iout(t)=

$$\frac{I_{o2} \cdot I_{b2}}{I_{d2}} - \frac{I_{o1}I - bI}{I_{dI}} +$$

$$L^{-1}\left[\frac{I_{o2}}{I_{d2}} - \frac{I_{o1}}{I_{dI}}\right] \frac{\left[1 + \frac{s\left(\frac{I_{o2}}{I_{d2}} - \frac{I_{o1}}{I_{dI}}\right)}{\frac{I_{o2}(c_1 \cdot nV_1)}{I_{dI} \cdot I_{d2}} - \frac{I_{o1}(c_2 \cdot nV_1)}{I_{dI} \cdot I_{d2}}}\right]}{\left[1 + \frac{s}{\frac{I_{d2}}{C_2 \cdot nV_t}}\right]\left[1 + \frac{s}{\frac{I_{dI}}{C_1 \cdot nV_1}}\right]} I_{in,ac}(s)$$

Equation 1

In Equation 1, Vt is the thermal voltage kt/q of the MOS transistors, n is a process parameter and $L^{-1}$ is the inverse Laplace transform. The meaning of the other terms is evident from FIG. 8C.

Equation 1 results in a broad passband frequency shaping network, suitable for the particular application. In the case when a tone-controller of the Baxandall type approximated by a "two-pole two-zero" function is needed, it can be implemented by feeding the input signal to the output of a log-domain lowpass 'biquad' and taking the difference as the output signal. A 'biquad' is a filter described by a biquadratic equation. The subtractor comprises transistors M2=M3=M4=M5 with W=2.4 um and L=2.0 um, and transistor M1 with W=10 um and L=2.0 um, for the appropriate dc output level to be realised.

The operation of the proposed circuit was simulated with SPECTRE models and AMS 2.0 um process parameters. FIGS. 9A and B show the effect of the tone control at low and high frequencies. The input current is of class-A having the formula Iin(t))=Ibias,[1+m sin(wt)], m being the modulation index. When Ibias=10 nA and the corner frequencies of the network is about 100 Hz and 12000 Hz, an input tone of 1000 Hz modulated by m=20, 30 and 40% exhibits a THD level of −58.2 dB, −55 dB and −56.2 dB respectively. For the same corner frequencies two equal amplitude sinusoidal tones with frequencies equal to 900 Hz and 1100 Hz and modulated by m=40% exhibited an InterModulation Distortion (IMD) level of −46.3 dB. (IMD is distortion produced when two signals are simultaneously applied to the filter.)

Thus a specific tone controller suitable for a micropower environment has been described by way of example. The circuit comprises two log-domain lossy integrators 221 and 222 and a subtractor 223 and takes advantage of the exponential behaviour of the MOS transistors when operated in weak inversion to match the characteristics of the Cochlea. The good dynamic range offered by the log compression coupled with flexible tuning adaptability are highly advantageous when attempting to realise an implantable analogue silicon device as a biological auditory prosthesis. The System described herein-above mainly focuses upon a new design of electronics architecture, resulting in smaller size and lower power consumption. The design is able to be applied to a multichannel CIS strategy and it also has the capability to provide a complex pulsatile stimulus to a short, single-channel electrode.

Remote Control

Figure 10:
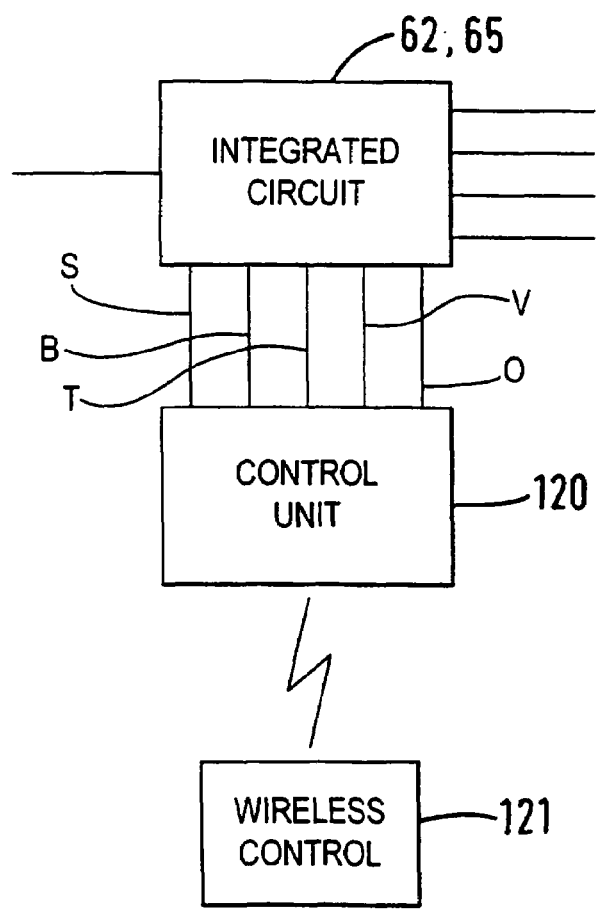
FIG. 10 is a schematic block diagram of a Hearing Aid or Cochlear Implant according to the invention and having a wireless remote control.

Referring to FIG. 10, the integrated circuit block 62 or 65 represents the parts of the embodiments of FIGS. 2 and 6 which are integratable into a single analogue chip. The chip has control inputs S,B,T,V, and O for sensitivity, bass, treble, volume and oscillator control. A control interface 120 provides control signals to operate the controls S,B,T,V, and O. The interface receives signals transmitted to it wirelessly from a remote commander 121.

Voltage to Current Converter

Figure 11:
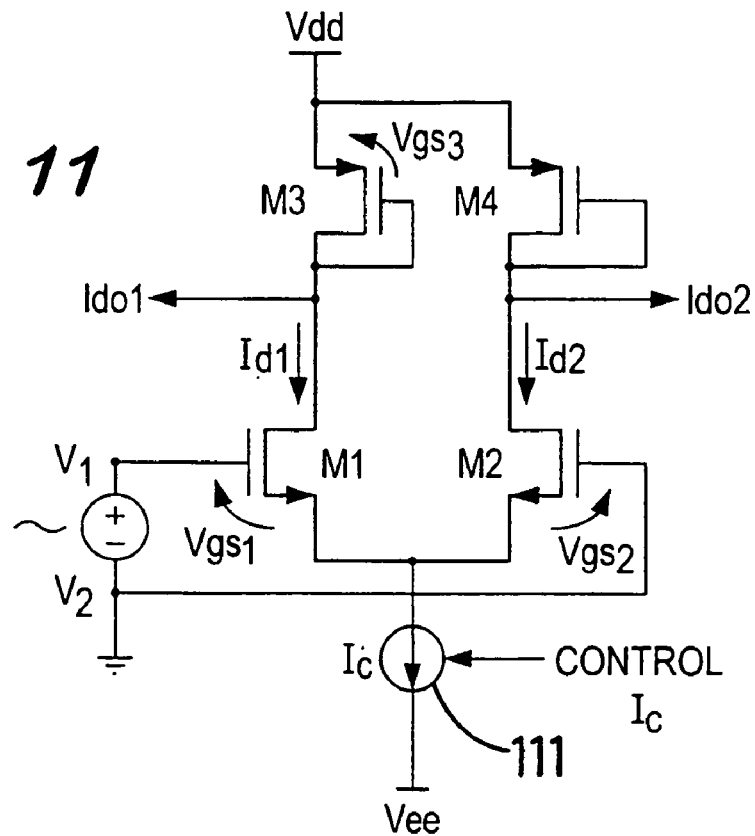
FIG. 11 is a diagram of the Voltage to Current converter of FIGS. 1,2 or 6.
Figure 12:
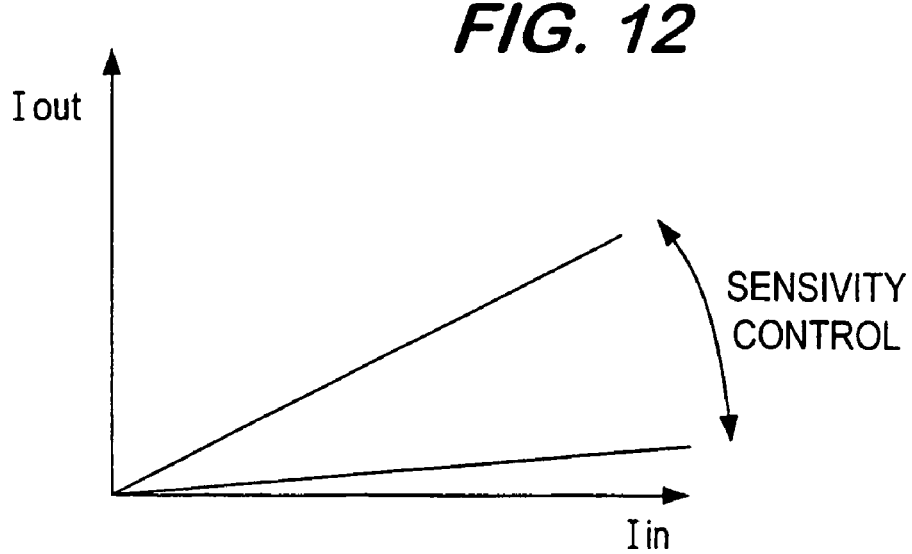
FIG. 12 is a diagram illustrating control of sensitivity.

FIG. 11 is a simplified circuit diagram of an example of the voltage to current converter 2, 22, 62 which compresses the dynamic range of the audio signal. The converter is an operational transconductance amplifier having an NMOS differential pair gain stage as known in the art. The converter has oppositely phased outputs $Ido_1$ $Ido_2$ at which currents proportional to the currents $Id_1$ and $Id_2$ are produced as required by the system of FIG. 6. If the converter is used in the system of FIG. 2, only one of the outputs is used. The converter has a current source 111. The current Ic through the current source 111 is varied to control the gain of the converter, and thus the sensitivity, as shown in FIG. 12.

The NMOS transistors are operating in weak inversion.

$$I_{d1} = \frac{I_c \cdot e^{+x}}{1 + e^{+x}}$$

$$I_{d2} = \frac{I_c \cdot e^{-x}}{1 + e^{-x}}$$

where $$x = \frac{V_1 - V_2}{n \cdot V_t}$$

where n is a process parameter and $V_t$=kT/q.

$Id_1$ and $Id_2$ are non-linear with a quasi-linear region. The non-linearity approximately matches the characteristics of the ear. The non-linearity outside the quasi-linear region compresses large current amplitudes to prevent over-stimulation of the Cochlear.

Band Pass Filter

FIGS. 13A to 13D are diagrams illustrating the construction and operation of one of the band-pass filters 101 of the system of FIG. 6. The band-pass filter is based on the work of Frey as described in [4], but is novel in itself.

Figure 13A:
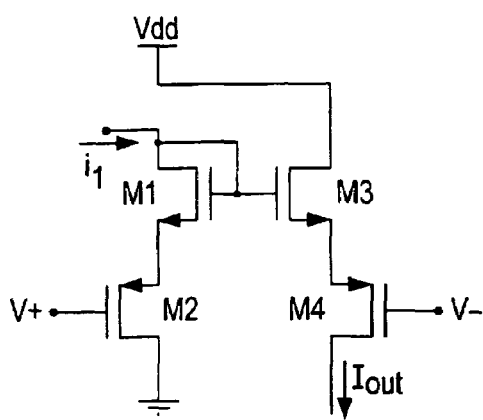
FIGS. 13A to D are diagrams of an example of a band-pass filter of the multi-channel Cochlear implant of FIG. 6.
Figure 13B:
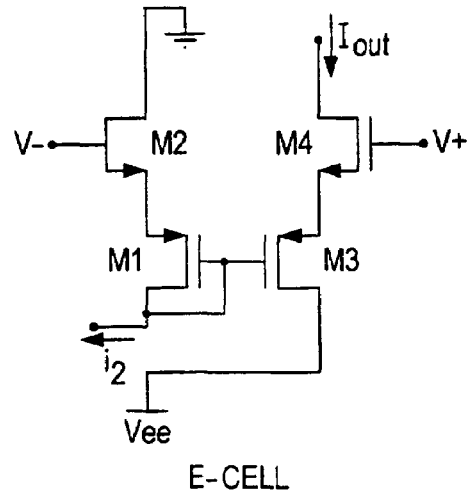

As shown in FIGS. 13A and 13B, basic units of the filter are an E+ cell and an E− cell. An E+ cell operates with the positive power supply and an E− cell operates with the negative power supply. Each cell is implemented in CMOS.

For both E+ and E− cells, the output current Iout(t) is related to the input current Iin(t) by $$I_{out}(t) = \left(\frac{W}{L}\right)_{M3,M4} \left(\frac{L}{W}\right)_{M2,M2} \cdot i_{in} \frac{V^+ - V^-}{e^{2n \cdot V_t}}$$

where M1, M2, M3, M4 are the transistors indicated in FIGS. 13A and 13B, W is the channel width, L is the channel length, and Vt is the thermal voltage kT/q.

Figure 13C:
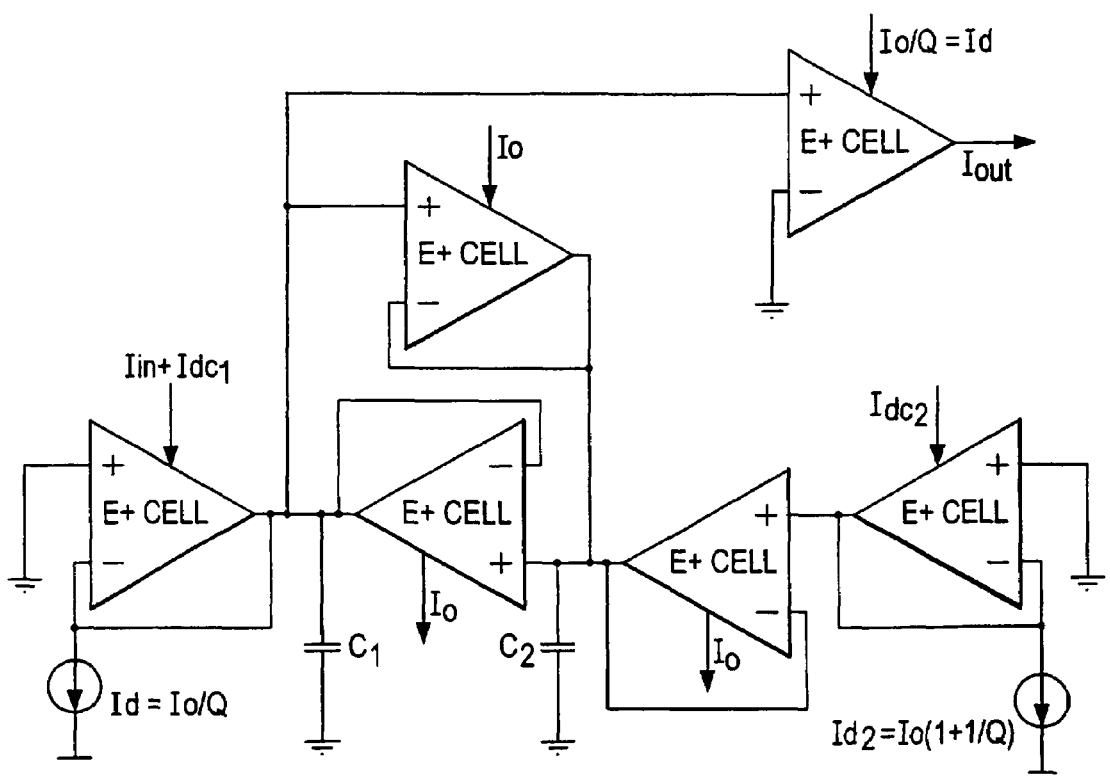
Figure 13D:
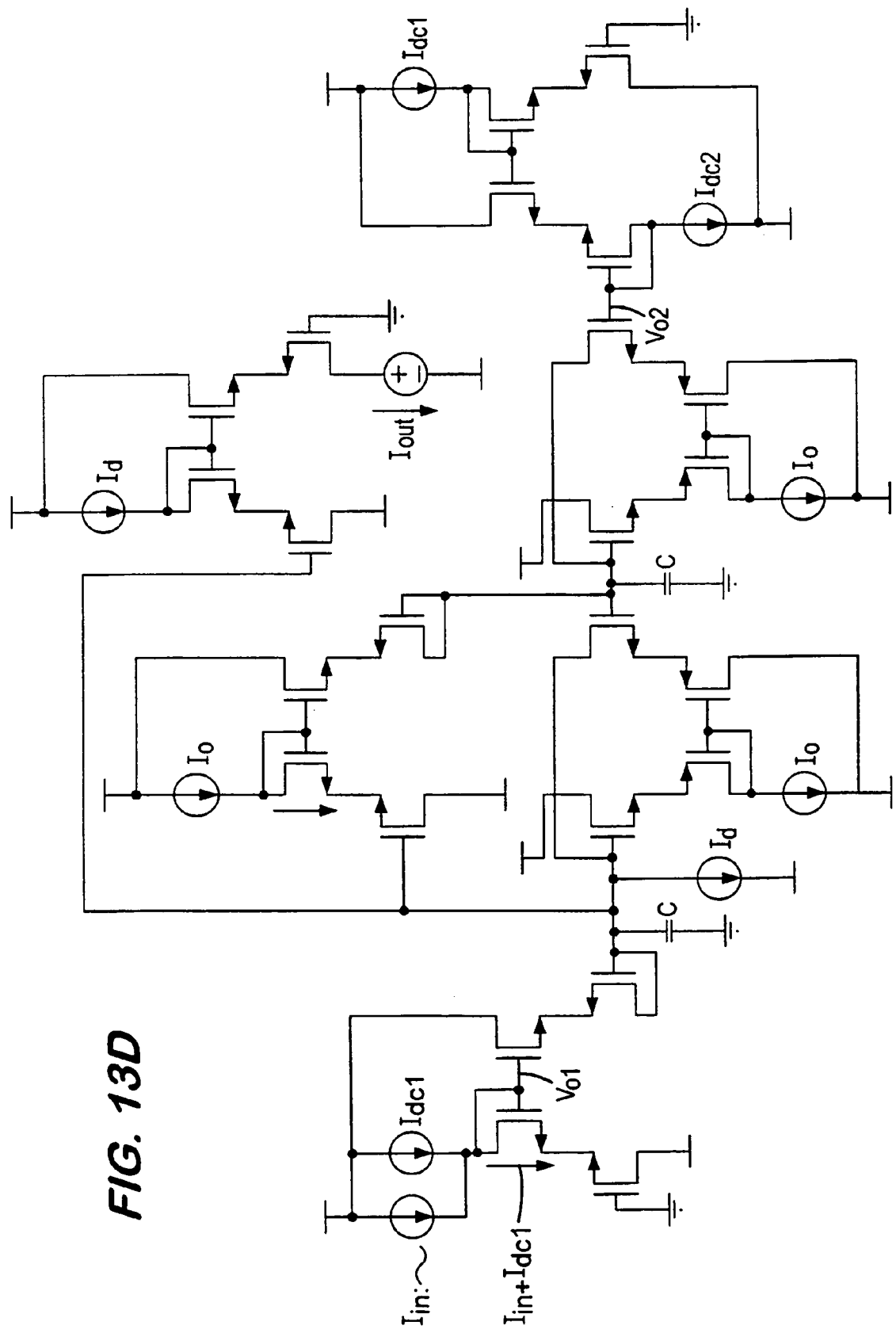

The E+ and E− cells are combined as shown in FIG. 13C to form a log-domain band-pass filter. The filter is shown in more details in FIG. 13D. In FIGS. 13C and 13D:—

Iin is the input current,

Iout is the output current, $Idc_1$ and $Idc_2$ are bias currents,

Io is a current defining the tuning frequency of the filter, n is a process parameter range between 1 and 1.5, and Q is the quality factor of the filter.

The transfer function of the filter is $$H(s) = \frac{I_{out}(s)}{I_{in}(s)} = \frac{\left(\frac{I_d}{C \cdot n \cdot V_t}\right) s}{s^2 + \left(\frac{I_d}{C \cdot n \cdot V_t}\right) s + \left(\frac{I_0}{C \cdot n \cdot V_t}\right)_s^2}$$

where Vt is the thermal voltage kT/q, and n is the process parameter.

The tuning frequency ωo of the filter is $\omega_0 = I_0/C \cdot n \cdot V_t$, $Q = I_0/I_d$, $I_d = I_0/Q$ $V_{o2} = 2 \cdot n \cdot V_t \cdot \ln[I_{dc2}/I_{dc1}]$, $I_{dc2} = I_0[1 + 1/Q]$, $Vo_1 = 2 \cdot n \cdot V_t \cdot \ln[(I_{in} + I_{dc1})/I_{do}]$ where Ido is the saturation current.

Alternative Multi-Channel Cochlear Implant

Figure 14A:
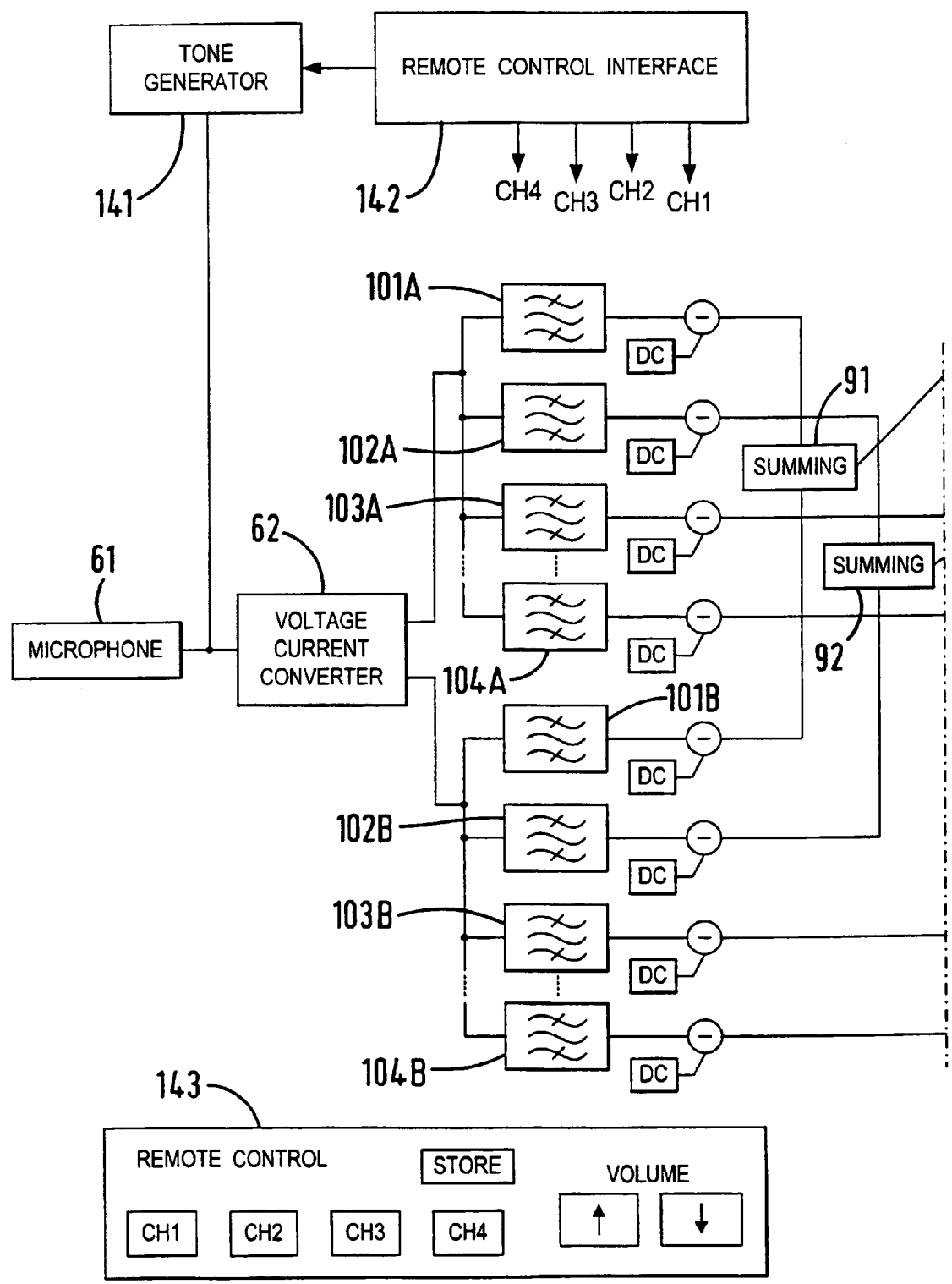
FIGS. 14A-B is another embodiment of a Cochlear Implant which opeates in the analogue domain.
Figure 14B:
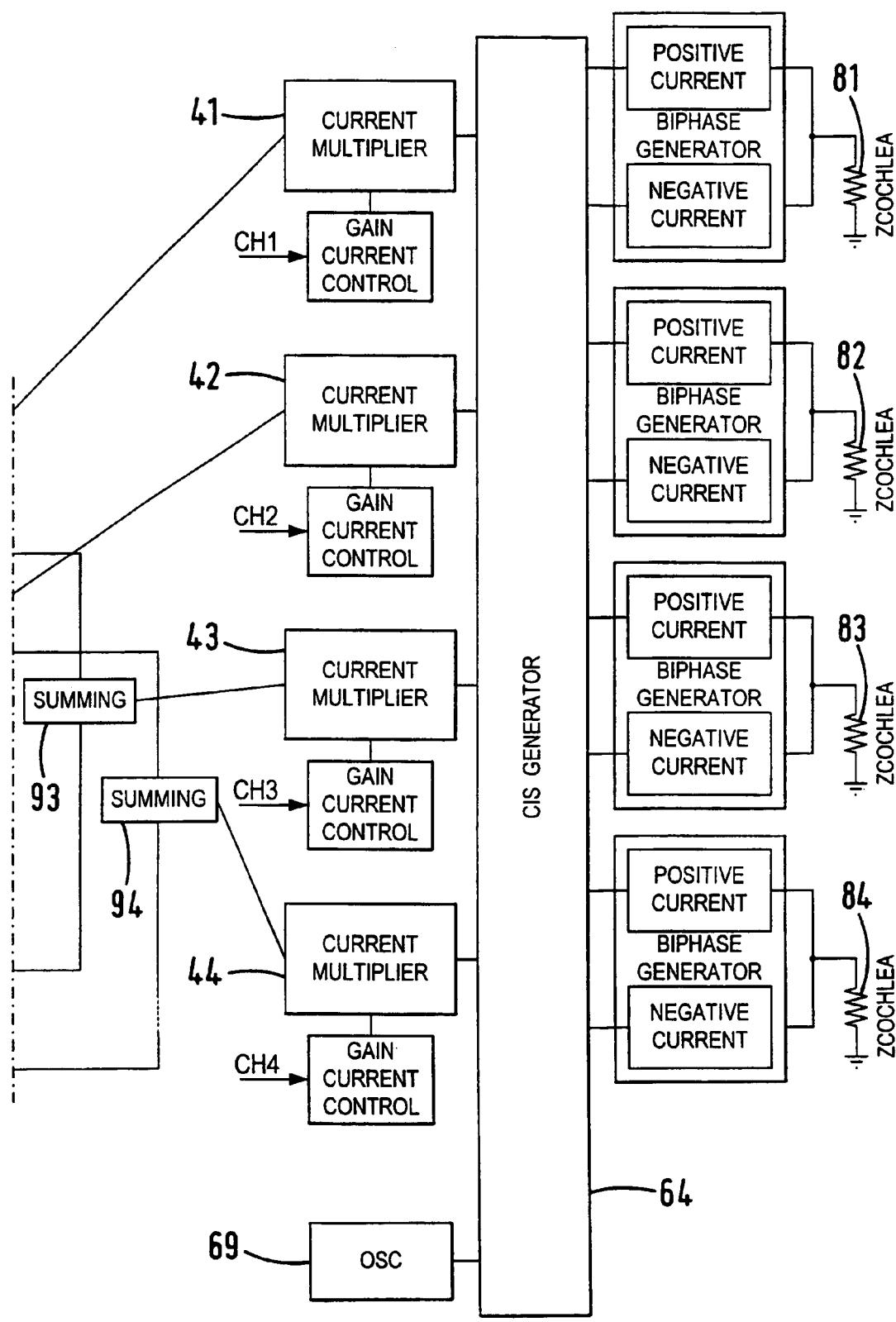

FIG. 14A-B shows another embodiment of a Cochlear Implant according to the invention and which also operates entirely in the analogue domain. The embodiment is a multi-channel embodiment having an array of electrodes 81 to 84 which in use are implanted in the ear. In the example of FIG. 14A-B only four channels are shown. In other examples there are at least two channels, and there may be more than four channels. A microphone 61, and compressor 62 similar to those of FIG. 2, produce compressed audio current signals. The compressor 62 is arranged to produce oppositely phased signals on respective outputs. The pair of unrectified opposite phase current signals are fed to respective arrays of band-pass filters 101A to 104A and 101B to 104B. Band pass filters 101A and B have the same filter characteristic and produce corresponding filtered signals of opposite phase. The other band pass filters 102A to 104A and 102B to 104B likewise produce correspondingly filtered signals of opposite phase. The band pass filtered signals are fed to half wave rectifiers 11, for example DC level shifting circuits. Corresponding half wave rectified signals of opposite phase are summed in adders 91 to 94 to produce full wave rectified signals which are amplified in respective current amplifiers 41 to 44. The fullwave rectified current signals produced by the amplifiers 41 to 44 correspond to different pass bands defined by the filters 101 to 104.

A circuit comprising MOS transistors, the transistors operating in weak inversion, is preferably used to implement the Band-pass filters 101 to 104 of FIG. 14. An example of a suitable circuit is described with reference to FIG. 13.

The fullwave rectified current signals produced by the amplifiers 41 to 44 are fed to an interleaving circuit 12 which samples the signals and interleaves the samples to produce Continuously Interleaved Samples which are biphase modulated and applied to the array of Cochlear Implant electrodes 81 to 84. An oscillator 69 produces a biphase square voltage wave. Referring to FIGS. 6 and 7, there are in effect four channels (in this example) associated with respective pass bands. One channel comprises the pair of band pass filters 101A and B the adder 91 and the electrode 81. The other channels likewise comprise a pair of band pass filters (102A,B; 103A,B; and 104A,B) an adder (92, 93, 94) and an electrode (82, 83, 84). Thus each of the electrodes 81 to 84 is associated with a respective one of the pass bands. The interleaving of the samples is controlled by the interleaving circuit 12. The interleaving circuit activates each channel in turn: when one channel is active all the other channels are inactive. Referring to FIG. 7, the circuit 12 sequentially connects: electrode 81 to filter 101A,B; the electrode 82 to filter 102A,B; the electrode 831 to filter 103A,B; and the electrode 841 to filter 104A,B etc. Each electrode receives a positive and a negative current pulse which together form one sample.

In accordance with this embodiment of the invention, a tone generator 141 is connected to the input of the compressor 62. The tone generator 141 and the current amplifiers 41 to 44 are controlled by a remote control system comprising a remote commander 143 operable by the patient and a remote control interface 142 which respond to control signals transmitted to it from the commander 143 to control the tone generator 141 and the amplifiers 41 to 44.

The tone generator is arranged to selectively generate respective tones at the fundamental frequencies of the filters 101 to 104. The tone which is generated is selected by the remote control system. The remote control system allows the volume of each channel of the Cochlear Prosthesis to be adjusted by controlling the gain of the current multipliers. The remote control 143 has channel selection buttons CH1 to CH4, a store button and one (or in this example two) volume control buttons. In this example there is one button for increasing volume and another for reducing volume. The patient selects one e.g. CH1 of the channels using one of the channel selection buttons. Selecting one channel CH1 mutes all the other channels CH2 to 4 by reducing the gains of the amplifiers 42 to 44 of the other channels to zero. Selecting one channel CH1 also causes the tone generator to generate a tone of preset amplitude having the fundamental frequency of the filter 101 of that channel. The patient then adjusts the gain of the amplifier 41 of the selected channel CH1 to a preferred value between the threshold and uncomfortable levels of hearing using the volume control buttons on the remote control. The interface 142 stores the selected value for example in response to actuation of the store button so that the setting is not lost when another channel is adjusted. Thus the patient has control of the programming of volume of the 'MAP'. The patient is preferably guided through the adjustment process by a skilled technician.

The fundamental frequencies of the filters are fixed in this example. The fixing of the fundamental frequencies may be done by a skilled technician when the prosthesis is first fitted to the patient. In other embodiments of the invention the filter frequencies may be adjusted by the user using the remote control system but such adjustment is currently considered to be too difficult for an unskilled user.

REFERENCES

[1] I. R. Sinclair, "Audio Electronics Reference Book", pp. 373-383 BSP Professional Books, 1989
[2] R. F. Graf & W. Sheets, "Encyclopaedia of Electronics Circuits", Vol. 6, pp. 653, Mc-Graw Hill 1996
[3] J. Markus, "Modem Electronics Circuits Reference Manuals", pp. 61, McGraw Hill 1980
[4] D. R. Frey, "Log-domain filtering: an approach to current-mode filtering", IEE Proceedings-G, vol. 140, pp. 406-416, 1993.
[5] D. R. Frey, "Exponential State-Space Filters: A generic current-mode design strategy", IEEE CAS-1, Vol. 43, No. 1, pp. 3442, 1996
[6] C. Toumazou, J. Ngarnmil and T. S. Lande, "Micropower log-domain filter for electronic cochlea", Electronics Letters, Vol. 30, No. 22, pp. 1839-1841, 1994.
[7] W. F. House, Cochlear Implants: "My Perspective"— Cochlear Implant Monographs.
[8] Horowitz and Hill, The Art of Electronics $2^{nd}$ Edition page 122
[9] J. Ngarnmil C. Tournazou, and T. S. Lande, "A fully tuneable micropower log-domain filter", 21st European solid State Circuits Conference ESSCIRC'95 France. September 1995.

The invention claimed is:

1. A multi-channel analogue audio signal processor for use with a cochlear prosthesis, comprising:
   an input for receiving an audio signal;
   a plurality of outputs for connection to respective ones of cochlear implant electrodes;
   a plurality of analogue signal processing channels coupled to the input, each channel comprising a tone control circuit comprising first and second log-domain filters having different low-pass bands and a subtractor for subtracting the output currents of the filters to produce a filtered signal, each of the filters comprising MOS transistors operating in weak inversion, and each of the filters being tuneable in the audio frequency range to adjust the low-pass cut-off frequency; and
   a tone generator for generating tones of preset amplitude and frequency dependent on the fundamental frequencies of the filters of the channels.

2. A processor according to claim 1, wherein each channel further comprises an amplifier having a controllable gain, the gain of which amplifier is adjustable by the adjustment means.

3. A processor according to claim 1, wherein the adjustment means includes a control interface for allowing adjustment of the gain of each channel in response to control signals transmitted by a wireless remote control.

4. A processor according to claim 3, further comprising tone generator control means for selecting the frequency of the tone produced by the tone generator.

5. A processor according to claim 4, wherein the tone generator control means comprises a wireless remote control.

6. A processor according to claim 1, where configured such that each channel is adjustable independently of all the other channels.

7. A processor according to claim 1, further comprising sampling means coupling the channels to the outputs.

8. A processor according to claim 7, wherein the sampling means comprises a continuous interleaved sample generator.

9. A processor according to claim 1, further comprising a plurality of biphase signal generators for supplying to the outputs biphase signals modulated by the output signals of the channels.

10. An analogue signal processor, comprising
an audio signal input;
an output for providing a processed audio output signal;
a tone control circuit coupling the input and the output and comprising first and second log-domain filters having different low-pass bands and a subtractor for subtracting the output currents of the filters to produce a filtered signal, each of the filters comprising MOS transistors operating in weak inversion, each of the filters being tuneable in the audio-frequency range to adjust the low-pass cut-off frequency; and
a full-wave rectification means for full-wave rectifying the processed audio output signal
wherein the tone control circuit further comprises third and fourth filters having low-pass bands substantially identical to the first and second filters respectively and a further subtractor for subtracting the output currents of the third and fourth filters to produce a further filtered signal, and the full-wave rectification means comprises means coupled to the input for producing oppositely-phased audio signals from the input signal, one of the oppositely-phased audio signals being supplied to the first and second filters and the other of the oppositely-phased audio signals being supplied to the third and fourth filters, half-wave rectification means for half-wave rectifying the filtered signals from the first mentioned and further subtractors, and a combiner for combining the half-wave rectified signals to effect full-wave rectification.

11. An analogue signal processor, comprising an audio signal input, an output for providing a processed audio output signal, a full-wave rectification means for full-wave rectifying the processed audio output signal, and a tone control circuit coupling the input and the output and comprising first and second log-domain filters having different low-pass bands and a subtractor for subtracting the output currents of the first and second filters to produce a filtered signal, each of the first and second filters comprising MOS transistors operating in weak inversion, and each of the first and second filters being tuneable in the audio frequency range to adjust the low-pass cut-off frequency, wherein the tone control circuit further comprises third and fourth filters having low-pass bands substantially identical to the first and second filters respectively and a second subtractor for subtracting the output currents of the third and fourth filters to produce a second filtered signal, and the full-wave rectification means comprises means coupled to the input for producing oppositely-phased audio signals from the input signal, one of the oppositely-phased audio signals being supplied to the first and second filters and the other of the oppositely-phased audio signals being supplied to the third and fourth filters, half-wave rectification means for half-wave rectifying the filtered signals from the first and second subtractors, and a combiner for combining the half-wave rectified signals to effect full-wave rectification.

12. A processor according to claim 11, wherein the third and fourth filters are log-domain filters comprising MOS transistors operating in weak inversion.

13. A processor according to claim 11, wherein the half-wave rectification means comprises means for applying a dc offset to the filtered signals.

* * * * *